United States Patent
Krahbichler

(10) Patent No.: US 11,278,388 B2
(45) Date of Patent: Mar. 22, 2022

(54) EMBOLIC PROTECTION DEVICE AND METHOD

(71) Applicant: SWAT Medical AB, Helsingborg (SE)

(72) Inventor: Erik Krahbichler, Helsingborg (SE)

(73) Assignee: SWAT Medical AB, Helsingborg (SE)

( * ) Notice: Subject to any disclaimer, the term of this patent is extended or adjusted under 35 U.S.C. 154(b) by 183 days.

(21) Appl. No.: 15/312,858

(22) PCT Filed: May 21, 2015

(86) PCT No.: PCT/EP2015/061340
§ 371 (c)(1),
(2) Date: Nov. 21, 2016

(87) PCT Pub. No.: WO2015/177322
PCT Pub. Date: Nov. 26, 2015

(65) Prior Publication Data
US 2017/0189160 A1    Jul. 6, 2017

Related U.S. Application Data

(60) Provisional application No. 62/001,349, filed on May 21, 2014.

(51) Int. Cl.
*A61F 2/01* (2006.01)
*A61B 17/12* (2006.01)
(Continued)

(52) U.S. Cl.
CPC .......... *A61F 2/01* (2013.01); *A61B 17/12172* (2013.01); *A61F 2/013* (2013.01);
(Continued)

(58) Field of Classification Search
CPC ...... A61F 2/01; A61F 2/013; A61F 2002/011; A61F 2002/015; A61F 2002/016;
(Continued)

(56) References Cited

U.S. PATENT DOCUMENTS 6,361,545 B1    3/2002    Macoviak et al.
2002/0133115 A1    9/2002    Gordon et al.
(Continued)

FOREIGN PATENT DOCUMENTS

EP    2693984 A2    2/2014
EP    2732794 A1    5/2014
(Continued)

OTHER PUBLICATIONS

WIPO, European International Search Authority, International Search Report and Written Opinion dated Jan. 9, 2015 in International Patent Application No. PCT/EP2015/061340, 15 pages.
European Patent Office, Supplementary European Search Report dated Sep. 25, 2019 in European Patent Application No. 19163802, 8 pp.

*Primary Examiner* — Ryan J. Severson
(74) *Attorney, Agent, or Firm* — Inskeep IP Group, Inc.

(57) ABSTRACT

A catheter device is disclosed comprising; an elongate sheath (503) with a lumen and a distal end for positioning at a heart valve (6), an embolic protection device (200) for temporarily positioning in the aortic arch for deflection of embolic debris from the ascending aorta to the descending aorta, said embolic protection device is connectable to a transluminal delivery unit (130) extending proximally from a connection point (131), and having: a frame with a periphery, a blood permeable unit within said periphery for preventing embolic particles from passing therethrough with a blood flow downstream an aortic valve into side vessels of said aortic arch to the brain of a patient, and at least one tissue apposition sustaining unit (300, 350) extending from said catheter, into said aortic arch, and being attached to said embolic protection device at a sustaining point (502), for application of a stabilization force offset to said connection point at said embolic protection device, such as at said periphery, and for providing said stabilization force towards an inner wall of said aortic arch, away from said heart, and
(Continued)

in a direction perpendicular to a longitudinal extension of said periphery, when said catheter device is positioned in said aortic arch, such that tissue apposition of said periphery to an inner wall of said aortic arch is supported by said force for improving stability and peripheral sealing. In addition related methods are disclosed.

7 Claims, 20 Drawing Sheets

(51) Int. Cl.
    *A61M 25/00* (2006.01)
    *A61F 2/24* (2006.01)
    *A61M 25/10* (2013.01)
    *A61M 25/06* (2006.01)

(52) U.S. Cl.
    CPC ......... *A61F 2/2427* (2013.01); *A61M 25/007* (2013.01); *A61B 2017/1205* (2013.01); *A61F 2/011* (2020.05); *A61F 2002/016* (2013.01); *A61F 2002/018* (2013.01); *A61F 2230/0008* (2013.01); *A61F 2250/0059* (2013.01); *A61M 25/1011* (2013.01); *A61M 2025/0681* (2013.01); *A61M 2025/1047* (2013.01)

(58) Field of Classification Search
    CPC .. A61F 2002/018; A61F 2/011; A61F 2/2427; A61B 17/12168; A61B 17/12172; A61B 17/12177; A61B 2017/1205
    See application file for complete search history.

(56) References Cited

U.S. PATENT DOCUMENTS

| | | | |
|---|---|---|---|
| 2002/0169437 A1* | 11/2002 | Macoviak | A61B 17/12136 604/509 |
| 2004/0073253 A1 | 4/2004 | Morrill et al. | |
| 2010/0179583 A1* | 7/2010 | Carpenter | A61F 2/013 606/200 |
| 2010/0324589 A1 | 12/2010 | Carpenter et al. | |
| 2013/0103075 A1* | 4/2013 | Wang | A61F 2/01 606/200 |
| 2013/0184739 A1* | 7/2013 | Brady | A61B 17/221 606/200 |
| 2014/0074148 A1* | 3/2014 | Glenn | A61F 2/24 606/200 |
| 2014/0074152 A1* | 3/2014 | Shezifi | A61F 2/01 606/200 |
| 2014/0243878 A1* | 8/2014 | Urbanski | A61F 2/01 606/200 |
| 2014/0257362 A1* | 9/2014 | Eidenschink | A61F 2/013 606/200 |
| 2016/0324621 A1* | 11/2016 | Shezifi | A61F 2/01 |

FOREIGN PATENT DOCUMENTS

| | | |
|---|---|---|
| EP | 2859864 A1 | 4/2015 |
| JP | 2003505216 A | 2/2003 |
| WO | WO 01/08743 A1 | 2/2001 |
| WO | WO2010/026240 A1 | 3/2010 |

\* cited by examiner

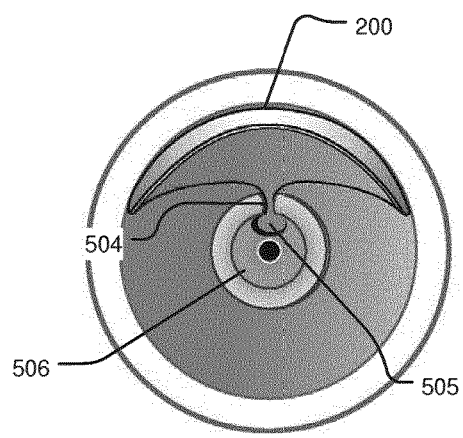
Fig. 18a
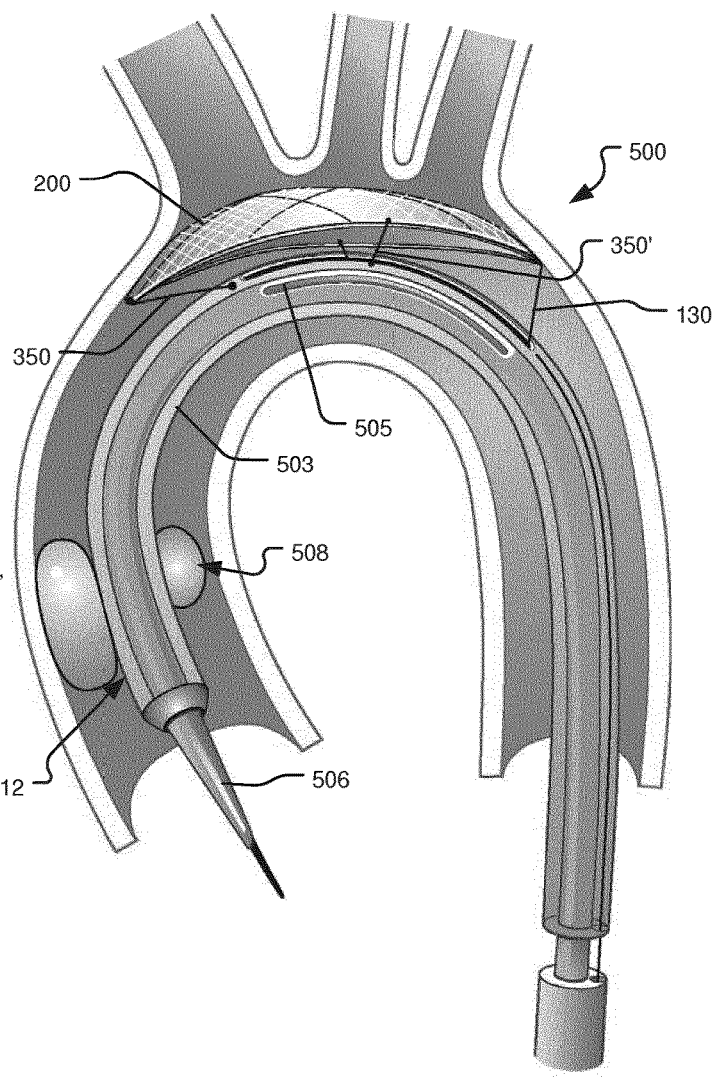
Fig. 18c
Fig. 18b
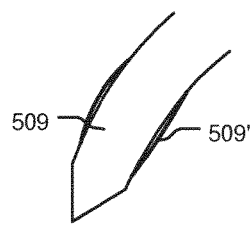
Fig. 18d
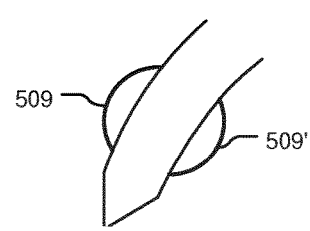
Fig. 18e

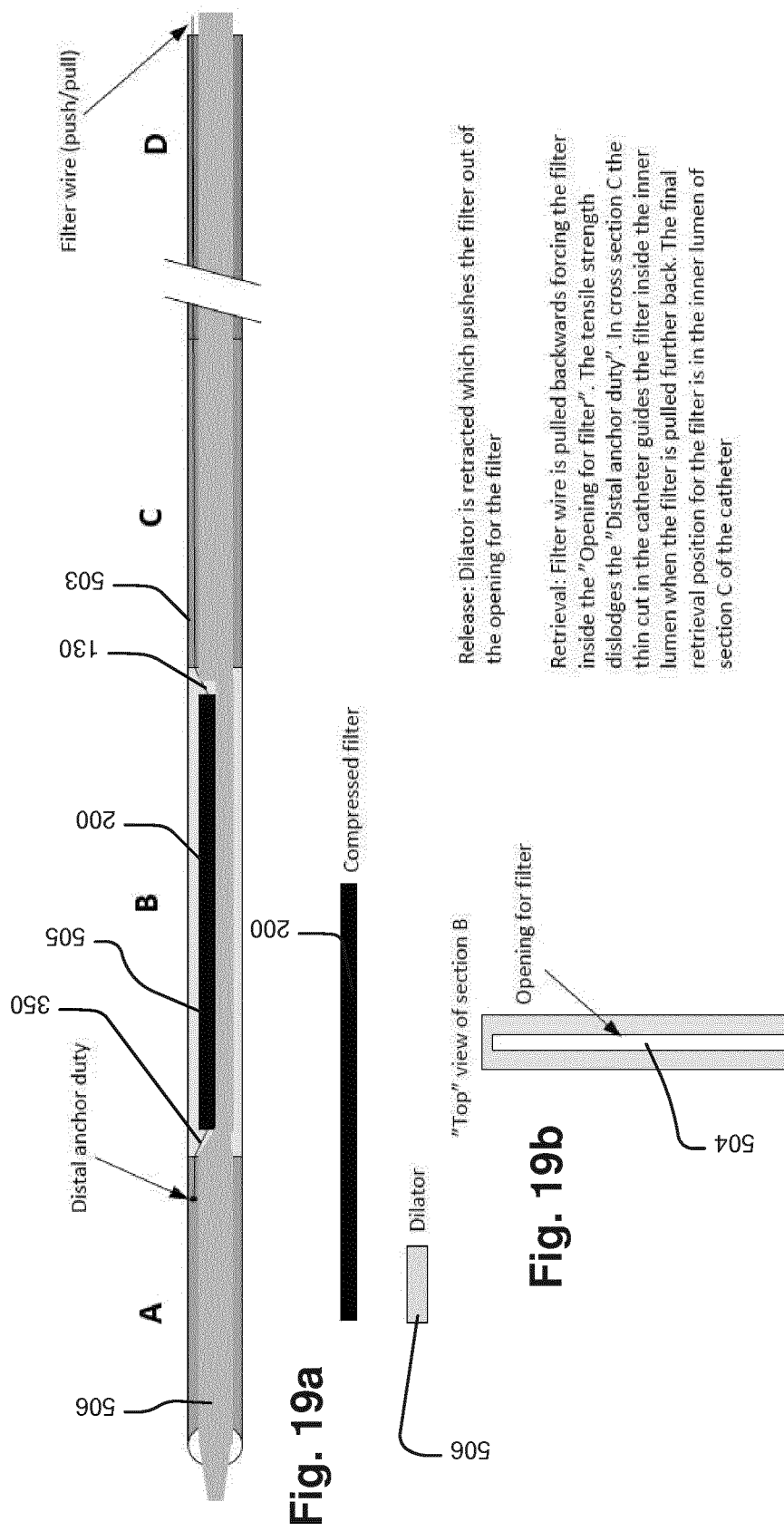

EMBOLIC PROTECTION DEVICE AND METHOD

RELATED APPLICATIONS

This application is the U.S. National Phase of and claims priority to International Patent Application No. PCT/EP2015/061340, International Filing Date May 21, 2015, entitled Improved Embolic Protection Device And Method; which claims benefit of U.S. Provisional Application Ser. No. 62/001,349, Filing Date May 21, 2014, entitled Improved Embolic Protection Device And Method; all of which are incorporated herein by reference in their entireties.

BACKGROUND OF THE INVENTION

Field of the Invention

This invention pertains in general to the field of embolic protection devices and catheters for procedures on the heart. More particularly the invention generally relates to devices, systems and methods for cerebral protection by deflection of embolic debris, during endovascular procedures, and introducers for such procedures, in particular procedures on the heart such as TAVI procedures or electrophysiology procedures or ablation procedures.

Description of Prior Art

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. Valvuloplasties are done endovascularly and percutaneous valve replacement is becoming an established procedure. Transcatheter Aortic Heart Valve (TAVI) is a procedure involving a collapsible aortic heart valve that can be manipulated into place with minimally-invasive techniques.

Cerebral embolism is a known complication of such endovascular procedures, and other cardiac surgery, cardiopulmonary bypass and catheter-based interventional cardiology, electrophysiology procedures etc. Embolic particles, may include thrombus, atheroma and lipids, plaque found in the diseased vessels and valves that is dislodged and results in embolization. Embolic particles may become dislodged by surgical or catheter manipulations and enter the bloodstream. Dislodged embolic particles can thus embolize into the brain downstream. Cerebral embolism can lead to neuropsychological deficits, stroke and even death.

Prevention of cerebral embolism benefits patients and improves the outcome of these procedures. Embolic protection devices should be compatible with the endovascular procedures, and for instance not hinder passage through the aortic arch to the heart.

Various embolic protection devices are known in the art. Some embolic protection devices are disclosed in WO 2012/009558 A2, or WO 2012/085916 A2, which are incorporated herein in their entireties for all purposes. However, these devices may provide iatrogenic damage to the vessels in which they are positioned, e.g. by bows or arms extending into the side vessels of the aortic arch. The bows or arms provide anchoring in the arch, but increase risk of scraping off embolic particles, in particular from around the ostia to the side vessels. The devices also have a rather high profile in the aortic arch, limiting the endovascular procedures to be performed through the arch.

More advantageous low profile planar devices for embolic protection of side branch vessels of the aortic arch have for instance been disclosed in WO 2010/026240 A1 or are described in international patent application number PCT/EP2012/058384, which was published after the priority date of the present application as WO2012152761, and which all are incorporated herein in their entirety for all purposes.

In WO2012009558 an umbrella shaped deflection device is disclosed having a delivery wire connected to a central hub. The device is delivered through one of the side vessels to be protected and the guide wire remains in the side vessel. The guide wire connected to the central hub may be pulled back to put the device into position. However, this leads potentially to so-called wind sucker disadvantages due to the movement of the aorta with every heart beat. Debris may collect at the edge of the umbrella and be occasionally sucked into the side vessel as the hub is locked when pulled back and does not follow the aorta movement sufficiently well. Embolic protection efficiency is thus not optimal of the devices described in WO2012009558.

In US2004/0073253A1 an embolic particle capturing is disclosed, which is positioned in the aortic arch via a femoral approach. A hoop at the distal end of the device has a larger diameter than the aorta at the implantation location and presses radially outwardly against the aortic wall. The device blocks the aortic arch when in position and does not allow for index procedures to be performed in a femoral approach.

In WO00/43062, a flow divider is described which compartments the aortic arch and seals the side vessel space from the latter. An embolic filter may be applied to blood perfused to the side vessel space, or filter the blood in the aortic arch in addition to the flow divider. However, the device is complicated as no blood can flow directly from the aortic arch to the side vessels and extracorporeal blood handling devices are needed.

In US 2002/0133115A1 methods for capturing medical agents are provided including magnets.

The devices of the state of the art may however be further improved. One issue is that blood, that may include embolic particles, may impair efficiency of the devices by bypassing across the device at the periphery thereof to the carotid arteries due to insufficient sealing at the periphery.

"Sailing" of the devices in the high pressure bloodstream ejected out of the heart is another issue avoided by examples of the present disclosure. The devices shall provide a stable positioning of the deflection device in the aortic arch.

A further problem with prior art devices is insufficient accuracy in positioning catheter devices such as introducers before performing the procedure, which increases the risk for complications and thereby reduced patient safety.

Hence, notwithstanding the efforts in the prior art, there remains a need for a further improved embolic protection devices of the type that can permit endovascular procedures, in particular of the heart, while protecting the cerebral vasculature during the procedures, and improved catheter devices such as introducers for such procedures.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing a device or method according to the appended patent claims for providing temporary embolic protection to a patient's aortic arch vessels during medical procedures, such as cardiac surgery and interventional cardiology and electrophysiology procedures. Embolic particles in the aortic blood flow are prevented from entering the aortic arch side branch vessels, including the carotid arteries that lead to the brain.

Disclosed herein are systems and methods for embolic deflection, including systems for deployment and removal.

According to one aspect of the disclosure a catheter device is disclosed comprising; an elongate sheath (503) with a lumen and a distal end for positioning at a heart valve (6), an embolic protection device (200) for temporarily positioning in the aortic arch for deflection of embolic debris from the ascending aorta to the descending aorta, said embolic protection device is connectable to a transluminal delivery unit (130) extending proximally from a connection point (131), and having: a frame with a periphery, a blood permeable unit within said periphery for preventing embolic particles from passing therethrough with a blood flow downstream an aortic valve into side vessels of said aortic arch to the brain of a patient, and at least one tissue apposition sustaining unit (300, 350) extending from said catheter, into said aortic arch, and being attached to said embolic protection device at a sustaining point (502), for application of a stabilization force offset to said connection point at said embolic protection device, such as at said periphery, and for providing said stabilization force towards an inner wall of said aortic arch, away from said heart, and in a direction perpendicular to a longitudinal extension of said periphery, when said catheter device is positioned in said aortic arch, such that tissue apposition of said periphery to an inner wall of said aortic arch is supported by said force for improving stability and peripheral sealing. In addition related methods are disclosed.

The frame may be elongate as shown in the Figures. The device 200 may thus be substantially planar. It can in specific examples further include a length to width ratio between 8:1 and 18:7. The device may vary in length from 10 mm to 120 mm, e.g., 25 mm, 45 mm, 60 mm, 75 mm, 90 mm, or 105 mm, and width from 5 mm to 70 mm, e.g., 10 mm, 20 mm, 30 mm, 40 mm, 50 mm, or 60 mm. The length of the device 200 may in particular examples be from approximately 80 mm to 90 mm, such as 80 mm, 82 mm, 84 mm, 86 mm, 88 mm, or 90 mm, or otherwise as may be necessary to approximate a distance between an upper wall of an ascending aorta, upstream of an opening of a brachiocephalic artery, and at an upper wall of a descending aorta downstream of an opening of a left subclavian artery. The width of the device 200 may be from 10 mm to 35 mm, such as 10 mm, 15 mm, 20 mm, 25 mm, 30 mm, or 35 mm, or otherwise as may approximate an internal diameter of the aorta. The term "substantially flat" may refer to a radius of curvature of no more than 80 mm, e.g., 0 mm, 5 mm, 10 mm, 20 mm, 30 mm, 40 mm, 50 mm, 60 mm, or 70 mm. The delivery unit 130 may also be pre-shaped to press against the top aortic wall lightly, thus allowing the device to remain along the vessel wall and clear of the passage of trans-femoral accessories that may be used in therapeutic cardiovascular procedures, e.g. TAVI procedures. This preshape may include a bend, e.g., 5°, 10°, 15°, 20°, 25°, 30°, 35°, 40°, 45°, 50°, 55°, 60°, 65°, 70°, 75°, 80°, 85°, or 90°, to further facilitate device deployment flush to the aortic vessel wall.

Connection point 131 can be used to connect the intravascular device 200 to a plunger, e.g., a plunger connected with a delivery wire disposed within a catheter. A locking mechanism with a latch may be provided at the connection point 131. A threaded attachment may be provided at the connection point 131 to attach the delivery unit. For instance a screw at the connection point can be mated with a screw on a plunger. Connection point 131 may include in an example a release and recapture hook for connecting the device 200 with a plunger. In some examples embodiments, a hook may include a latch or wire strand that may be part of the device 200. In other examples, the blood permeable unit, catheter, or delivery wire may end in a loop and may be threaded through a latch. When so threaded, a wire or catheter fitted with a looped end may be clicked into a hook and may securely push the device into place or pull the device out of position from the aorta. In some examples, the hook may end in a ball-tip so that strands from the blood permeable unit do not fray or unravel or scratch the vessel wall or the inner tube of a catheter. In other embodiments, a clasp at an end of the device may be pressed into or onto a clasp at, for example, an end of a catheter or delivery wire, and the two clasps may be joined by such pressing.

In still other example, the device 200 may be adapted for use with other embolic protection devices, e.g., those described in U.S. Pat. Nos. 8,062,324 and 7,232,453, each of which is hereby incorporated by reference in its entirety for all purposes.

In some embodiments, the device may be rotated clockwise or counter-clockwise respectively.

The device further includes at least one tissue apposition sustaining unit, which is not a delivery shaft or guide wire of the device. The tissue apposition sustaining unit is provided for application of a force offset to the connection point at the device. The force may be called a stabilization force as the force contributes to a secure positioning of the embolic protection device in the aortic arch. Offset to the connection point may for instance be at the periphery. It may also be adjacent the periphery. It may also be centrally of the blood permeable unit within the periphery. The force is applied or directed towards an inner wall of the aortic arch when the device is positioned in the aortic arch. In this manner tissue apposition of the periphery to an inner wall of the aortic arch is supported by the force. For instance, a tractive force such applied may pull a periphery of the device against the inner wall. The tractive force may be applied against a delivery catheter or the like and lifts the embolic protection device against the aortic wall, in a direction away from the heart, preferably a coronal direction ("upwards"/toward the patient's neck or head). The (stabilization) force supports locking the device in place upon implantation.

The embolic protection device can thus be reliably placed across the apex of the aorta in order to prevent emboli from flowing into the carotid arteries. The inventive solution is not iatrogenic, as it prevents creation of debris from e.g. ostia of side vessels. Iatrogenic relates to an adverse condition in a patient resulting from treatment by a physician or surgeon. Arms, anchors, delivery shafts, bows, etc. of inferior embolic protection devices, for instance extending into the side vessels, risking scraping off of plaque from the inner vessel wall or ostia, are not needed and can be avoided thanks to the present disclosure.

Embolic particles, are efficiently prevented from bypassing across the device at the periphery thereof to the carotid arteries thanks to improved sealing at the periphery. "Sailing" of the devices in the high pressure bloodstream ejected out of the heart avoided. A stable positioning of the deflection device in the aortic arch is provided.

The embolic protection device may preferably be a deflector for deflecting embolic particles. Alternatively, or in addition, it may be a filter for catching embolic particles.

The device may in examples be deliverable via a side channel catheter, e.g. via a femoral approach. Such as side channel catheter is described in PCT/EP2012/0058384, which was published after the priority date of the present application as WO2012152761, and which is incorporated herein by reference in its entirety for all purposes. The catheter may further be improved by multiple side channels, one for the embolic protection device. Tethers may run in the same channel or other channels of the catheter. A pigtail catheter may be provided in such an auxiliary side channel. The pigtail catheter may be used to further stabilize the catheter against the annulus of the aortic valve and/or inner wall of the aortic arch, such as described in WO 2012/094195 A1, which is incorporated herein by reference in its entirety for all purposes, see in particular FIGS. 10A and 10B of WO 2012/094195 A1 as well as related description passages in WO 2012/094195 A1.

The device may in examples be deliverable via a side vessel, such as described in WO 2010/026240 A1.

The device may in examples be deliverable via the aorta, e.g. in a direct aorta approach, such as described in concurrently filed US application of the same applicant with the title "METHOD FOR DELIVERY OF AN EMBOLIC PROTECTION UNIT" and it's priority application with application No. U.S. 61/726,540 filed 14 Nov. 2012. Both applications are herein incorporated herein by reference in their entirety for all purposes.

The aforementioned force, also called stabilization force, may include or be a tractive force. The apposition sustaining/supporting unit may then be an active traction unit that for instance has at least one operable tether 300 distally connected at the location offset the connection point 131. The distal connection location 310 of the traction unit or tether may be located at the frame 133, periphery 180 and/or blood permeable unit 132, of the embolic protection device 200 for providing the tractive force to the device. The tether 300 has one or more distal end(s). The distal end is for instance connected to the periphery 180 of the embolic protection device 200. The tether's 300 distal end(s) may be connected to the blood permeable unit 132, such as a filter or deflector membrane. The membrane may be moved by the traction, e.g. if the membrane is flexible and/or elastic. Thus the traction may lift the membrane.

Tether(s), or more precisely, tetherline(s) are provided to control a sealing degree of the periphery. Tether(s) are provided for direction of apposition towards aortic tissue/cerebral arteries. The tether may provide active traction by a pull action on the tether communicated to the embolic protection device to which it is distally connected. The traction force may be different than a pulling force of a delivery device of the embolic protection device, thus advantageously avoiding a windsucker effect as the forces may be chosen so that the periphery of the device follows the aortic arch movement to a larger degree than its attached delivery device.

The tether is movable relative the delivery unit 130. The delivery unit 130 provides in these examples a counter point for being able to apply the stabilization force, e.g. like a Bowden cable principle. Alternatively, or in addition, for instance a collection device in form of a conical filter co-axially arranged around the delivery device in use anchored in the side vessel may provide a counter point for being able to provide the needed stabilization force to the embolic protection device. In this manner, the device 200 is positionable in the aortic arch so that the delivery device may be locked in a "delivered" position, e.g. at its proximal end at or outside a port of an introducer. The tether may then still be movable and improve sealing as described herein.

In any of the devices of the invention, the delivery unit 130 may also include a preformed bend, such as shown in FIG. 1. The preformed bend can be between 5° and 90°. In some aspects, the device 100 also includes a filter (not shown), e.g. expandable from the exterior of the catheter 160, proximal to the transluminally deliverable embolic protection device 200 for temporarily positioning in the aortic arch, and also, e.g., proximal to the preformed bend. The filter can be sized to filter a side branch blood vessel. A delivery unit 130, such as a central member at the transluminally deliverable embolic protection device 200, can thus pass through the second filter. The filter can have the capability of preventing particles from passing from the aortic arch downstream the side vessel. The filter may be expandable for engagement into the vessel wall of the side vessel. It may provide for a fix point allowing the application of the traction force while preventing disadvantages related to the windsucker effect. The filter may be conical in shape with a catheter and/or delivery wire passing through the apex of the filter. The filter may also be substantially flat with the catheter and/or delivery wire passing through any point within the filter so long as the catheter and/or delivery wire is connected to the filter, e.g., at all points along the catheter's or delivery wire's outer perimeter. The width of the widest portion of the filter may be pre-sized and preformed to accommodate particular subclavian arterial anatomy, e.g., 2, 4, 6, or 8 mm in width. Other shapes may be used.

Tether(s) may be multifilament(s) tether(s), which provides for a particularly flexible solution advantageous for narrow lumen navigation.

A tether may extend straight across the blood permeable unit to the forward end of the device. Thus the middle line may be pulled up and the periphery is tensioned against the inner wall. The tether provides for a lifting force to the forward end. In case the tether is guided at the middle line, e.g. threaded through eyelets, it may provide a progressive lifting force distributed along the device, which allows for particular effective sealing and/or stabilization at the periphery.

The at least one tether may be longitudinally elastic, i.e. it is longitudinally stretchable and resiliently return to a non-stretched longitudinal extension. The tether may be elastic along its entire length. The tether may include one or more elastic portions or elastic elements. The elastic portion may be a helical wound portion of the tether acting as a spring. The elastic portion may be a tubular braid of a double helically wound strands. The elastic portion may be made of an elastic material, preferably biocompatible, like rubber. In this manner the tractive force is variable. This may be advantageous for preventing rupture of the tether line as a non-linear extension may be "felt" by an operator. This variable traction force may also be advantageous if the tether is tension, applying a desired traction for improving sealing of the embolic protection device. The tether may be locked at its proximal end in this position, e.g. extending out of an introducer port. The elasticity may provide for compensating physiological movements of the aortic arch relative a proximal end of the device and/or tether while maintaining the tissue apposition. Issues related to the afore described windsucker effect are avoided. The applied force is provided within a certain range suitable to maintain the improved peripheral sealing while the aortic arch moves due to the beating heart and blood pulse waves.

The blood permeable unit may have at least one guiding unit, such as an eyelet, a tubular bent element, a roller, etc. The guiding unit may receive the tether proximally its distal end where it is attached to the device, such as at the blood permeable unit, flange, or periphery. The guiding units, such as eyelet(s) etc. provide for locally controllable apposition at the device. The traction force may be distributed to different areas of the device.

The device may have an attachment point where a distal end of the tether is connected to the device and a tractive force is transmissible via the attachment point to the device towards the periphery. Optionally a radiopaque one or more fiducial markers may be provided at the device. A fiducial marker may be provided at the attachment point. Fiducial markers provide for advantageous X-ray visibility and navigation, position feedback and control of the device.

In some examples, the tether is proximally extending through an ostium into a selected side vessel such that the tractive force centers the device in relation to the ostium. When pulling the tetherline, it pulls the device at its periphery against the inner wall of the aorta for locking the device in place. In this manner the device is self aligning in relation to the ostium of the selected side vessel thanks to the tether. The skilled person may provide suitable guiding units for the tether when reading this disclosure to obtain this function.

The device may include multiple tethers distally attached along the periphery. Alternatively, or in addition, a single proximal tetherline may separate distally into a plurality of (sub)tetherlines. For instance, a tether may be branched in the form of a Y. A single tether to be operated proximally may then distribute a tractive force distally via its two distal end points to the embolic protection device. An example with a plurality of endpoints is shown in FIG. 8. Multiple tethers may be used or combined with tethers having multiple distal ends. The multiple tethers may be collected proximally at the device, e.g. at a base thereof. In this manner, the device provides for a progressive force that is evenly distributed along the periphery of the device. The device may in this manner advantageously adapt to the inner shape of the aortic arch. The adaptation may even more enhanced by providing longitudinally elastic portions at the tether(s). For instance, the branched (sub)tetherlines may be provided of elastic material, while the main line is substantially non-elastic, but flexible.

In some examples, the device may have at least one rib extending between different, preferably opposite, joints at the periphery, wherein the tether is distally attached at the rib. The tether may thus apply a tractive force to the rib(s), which in turn transfers the force to the periphery of the device towards the aortic inner wall tissue. The rib may be a beam or yoke. It may be arranged longitudinal or transversal in relation to the expanded device's longitudinal axis. There may be a plurality of such ribs in a device. Devices having multiple petals or wings may have one or more ribs on one or more of the petals or wings to obtain a favourable force distribution. The rib may be capable of providing structural support to the device. The term "provide structural support" refers to the property contributing to shape and stiffness of the device. The stiffness of the intra-vascular device 200 will be determined by the stiffness of the blood permeable unit, the periphery, and/or radiating supporting members. For example, the device 200 can be stiffened by the inclusion of heavier gauge wire or by the inclusion of stiffer central member, yoke, or radiating supporting members. Furthermore, multiple wires of a certain gauge can be wound together to increase the stiffness of the device, e.g., the device can include 2, 3, 4, 5, or more wires to increase the stiffness of the intra-vascular device 200.

For instance a petal or wing of the device may be arranged upstream in relation to the aortic blood flow. Alternatively, or in addition, the device may have a petal or wing of the device may be arranged downstream in relation to the aortic blood flow. One or more, or each of the petals or wings may have tissue apposition sustaining unit(s), like tethers, pushers, springs as described herein. It may be sufficient to provide petals or wings arranged upstream in relation to the aortic blood flow with tissue apposition sustaining unit(s). Petals or wings arranged downstream may be sufficiently pushed against the aortic inner wall tissue by the pulsatile blood flow in the aorta passing along the blood permeable unit of the device. However, having tissue apposition sustaining unit(s) at petals or wings arranged in downstream direction from a connection point may advantageously be supported by such tissue apposition sustaining unit(s) during pressure changes in the aorta. The aortic pressure is lower during the diastolic phases and may tend to be more leaky than during systolic phases. The tissue apposition sustaining unit(s) may be dimensioned to be sufficient supportive during diastole, and thus be more advantageous (smaller, less mass) for insertion into the body than being dimensioned for systolic pressure support.

The tissue apposition sustaining unit(s) may limit movement of the blood permeable unit caused by the pulsatile blood flow. The abovementioned "sailing" of the device is this limited or avoided by the tissue apposition units(s). For instance having a rib may provide for this limited movement range. The rib and/or tether limit movement of the blood permeable unit. Having connected a tether to the device may provide then for a progressive traction force and particularly improved sealing as forces on the periphery caused by pulsatile pressure changes are evenly distributed during heartbeat's pulsatile flows.

The rib may be a yoke, such as extending proximally above the blood permeable unit. "Above" means on the filtered side of the unit downstream the blood flow passing the unit. "Below" means consequently in that context the opposite side. The yoke may preferably extend in a longitudinal direction of at least a portion of the device. The distal tether end(s) may be directly attached to the rib. The distal tether end(s) may be guided by guiding units(s) at the rib to the to periphery, providing an advantageous distribution of tractive force. An "above" positioned rib may at the same time limit movement of the blood permeable unit, thus avoiding contact with tissue, e.g. ostia and avoids generation of debris by such avoided contact. Device of examples of the present disclosure can include additional rib members that are located above and/or below a selectively permeable unit 132.

The device may include multiple tethers, or a single tether splitting distally into multiple strands. In an example two tethers or strands are distally attached to the periphery in a Y-shape from a base of the device.

The device may include at least one eyelet, wherein one or more of the tethers are threaded through at least one eyelet. An eyelet may preferably be provided at a pivot point and/or at a base of the device. Contact of the tether with tissue, e.g. ostia is thus avoided thanks to the eyelets and generation of debris is avoided by preventing contact of the tether with tissue when tensioned.

The blood permeable unit may be flexible. It is for example a flat (substantially planar) membrane with defined porosity or holes. A tether may be distally attached to the membrane. A traction force thus applied may raise the membrane out of a plane of the membrane, such that for instance to a volcano shape, including the attachment location of the tether to the membrane at the to thereof. The volcano shape may be advantageously increasing the efficiency of the device. The top of the volcano shape may be arranged to extend into an ostium, into a portion of a side vessel. Trapping of particles may thus be provided by the interior funnel shape of the volcano into which blood flows. Increased filter efficiency will be the result.

The traction unit may alternatively or additionally include a passive traction unit. The passive traction unit is not operated by an operator, but provides automatically for the stabilization force and improved peripheral sealing. The passive traction unit may be a spring. It may have a shape memory element for instance activated by body temperature, such as a portion of the frame, for providing the tractive force relative a delivery portion or device. For instance the device may include "winglets" extending from the periphery of the device which have a shape memory. Another example is shape memory springs that are activated to tension tethers, e.g. from a base of the device. A portion of a tether may be provided as a shape memory portion. Such tether may be delivered in an elongate shape and then change to a memory induced shape, shortening the tether to provide the tensile force. The memory induced shape may be a helical coil shape additionally allowing for elasticity of the memory activated tether, particularly advantageous for pressure and/or movement compensations.

The device may have a flange unit extending radially outward from the periphery of the device, e.g. from the frame. The flange unit may be angled in relation to a plane of the blood permeable unit for a pre-tension against which the tractive force is provided. The flange unit may provide for further improved sealing as sealing is supported by the blood pressure in the aorta. The flange unit may be made of a fabric. The fabric may be woven. The fabric may be woven from PTFE threads providing for advantageous sealing and biocompatibility. The fabric may be arranged as a collar around the frame of the device. The collar may extend in a direction opposite to a filter membrane attached to the frame. The flange unit provides for avoiding recesses at the periphery of the device towards the inner wall tissue. This is particularly advantageous as embolic particles may collect in such recesses. These collected particles may then be flushed into the side vessels when the device is removed. Avoiding particles collecting at the periphery reduces this potential issue.

The tissue apposition sustaining unit may include a pushing unit, and the force includes a pushing force, against the frame, periphery and/or blood permeable unit. The pushing unit provides the pushing force and presses the periphery to the inner wall.

The tissue apposition sustaining unit may include a magnetic element and the force includes a magnetic force.

According to another aspect of the disclosure, a method (900) of positioning an catheter device (500) in the aortic arch, is disclosed comprising transluminally delivering (901) an embolic protection device (200) such as a deflector and/or filter, in the aortic arch, said embolic protection device connected to a transluminal delivery unit (130) extending proximally from a connection point (131) of said embolic protection device; positioning (902) said embolic protection device in said aortic arch, including expanding (903) a frame of said device and flattening a blood permeable unit in said aortic arch, bringing (904) a periphery of said embolic protection device in apposition with an inner wall of said aortic arch to cover ostia of side vessels at least including the carotid arteries for preventing embolic particles from passing therethrough into side vessels to the brain of a patient; and applying (905) a stabilization force by at least one tissue apposition sustaining unit (300, 350), extending from said catheter, into said aortic arch, and being attached to said embolic protection device at a sustaining point (502), wherein said force is applied offset to said connection point at said embolic protection device, such as at said periphery, and is directed towards an inner wall of said aortic arch providing said stabilization force towards an inner wall of said aortic arch, away from said heart, and in a direction perpendicular to a longitudinal extension of said periphery, when said catheter device is positioned in said aortic arch, such that tissue apposition of said periphery to an inner wall of said aortic arch is supported by said stabilization force for improving stability and peripheral sealing. In this manner tissue apposition of the periphery to an inner wall of the aortic arch is supported by the force.

This method is less iatrogenic than known methods. It provides for improved sealing of the periphery of an embolic protection device. It further prevents creation of debris from an ostium in the aortic arch.

The supported apposition is improving apposition of the periphery to the inner wall of the aortic arch, such that the improved apposition provides for improved sealing of the periphery against the inner wall.

The force may be applied in a substantially proximal direction relative the device for the improved sealing.

Applying the force may include applying a tractive force by a traction unit. The tractive force may include pulling a periphery of the device against the inner wall for locking the device in place in the aortic arch. The tractive force may be applied by at least one tether distally connected to the frame, periphery and/or blood permeable unit for providing the tractive force.

The device may be delivered to the aortic arch via one of the side vessels, such as the brachiocephalic artery from the right subclavian artery, the left carotid artery, or the left subclavian artery. It may be delivered to the aortic arch via the descending aorta such as in a femoral approach, e.g. in a side channel of a main catheter. It may be delivered to the aortic arch through the wall of the ascending aorta, which is an approach called "direct aorta" approach.

According to another aspect of the disclosure, a method (1000) of preventing emboli flowing in the aortic arch from entering side branch vessels thereof, including advancing (1001) an embolic protection to said aortic arch; and manipulating (1002) the protection device such that it covers the ostia of each of the side branch vessels, including applying (1003) a force to said protection device for improving sealing of said device at a periphery thereof, including applying a force offset to a connection point at said device by a distal guide element (350) connected between a distal sustaining point of said embolic protection device and a distal connection point (501) on a catheter; wherein the protection device permits blood flow from the aortic arch into each of the side branch vessels, but prevents emboli from entering the first and second side branch vessels without obstructing the lumen of the aortic arch.

According to a further aspect of the disclosure, a method for limiting the flow of emboli into the carotid arteries from the aorta, is provided. The method includes delivering an embolic protection device to the aortic arch to extend between the ascending aorta and the descending aorta to position the embolic protection device or components thereof into the aortic arch to prevent embolic debris to enter the carotid arteries. Further, it includes proximally tensioning at least one tether member distally connected to the embolic protection device, thus controlling a degree of apposition and fluid sealing of the embolic protection device against the inner vessel wall of the aortic arch.

According to a still further aspect of the disclosure, a method (1100) for performing an endovascular procedure on a heart, the method including: delivering (1101) an embolic protection device to the aortic arch through one of the following vessels: the brachiocephalic artery from the right subclavian artery, the left carotid artery, the left subclavian artery, or the descending aorta such as in a femoral approach; or through the wall of the ascending aorta; to position embolic protection device into the aortic arch to prevent embolic debris to enter the carotid arteries, applying (1101) a stabilization force to said protection device for improving sealing of said device at a periphery thereof, including applying a force offset to a connection point at said device by at least one tissue apposition sustaining unit, not being a delivery shaft of said device, thus controlling a degree of apposition and fluid sealing of the embolic protection device against the inner vessel wall of the aortic arch by said force; and delivering (1102) a first catheter through the descending aorta, the left subclavian artery or the aortic vessel wall at the aortic arch to the heart to effect at least a step related to the endovascular procedure on the heart applying (1103) said stabilization force by tensioning at least one distal guide element (350) connected between a distal sustaining point of said embolic protection device and a distal connection point (501) on a catheter, wherein said delivering said first catheter includes placing a balloon mounted on said first catheter with expanding said balloon in the ascending aortic arch.

The step of applying the force may includes proximally tensioning at least one tether member or pushing unit distally connected to the embolic protection device.

The step of delivering the embolic protection device may be made transluminally, and delivering the first catheter may be performed after the delivering the embolic protection device.

Delivering the first catheter may include placing a balloon mounted on the first catheter with expanding the balloon in the ascending aortic arch to lock a distal end of the first catheter in place. The balloon may have a donut shape having a filter between the catheter and the inner ring of the donut shape.

The embolic protection device used in the method may extends from a distal end of a second catheter or separate channel of the first catheter, such that the position of the embolic protection device can be independently adjusted from the position of the first catheter.

Delivering a first catheter may be performed concurrently with delivering the embolic protection device via a separate channel of the first catheter, independent of the endovascular procedure.

The endovascular procedure on the heart may includes at least a step related to removal of a heart valve, the placement of a prosthetic heart valve, or repair of a heart valve. The embolic protection device may be removed from the aortic arch following performance of the endovascular procedure.

Further embodiments of the disclosure are defined in the dependent claims, wherein features for the second and subsequent aspects of the invention are as for the first aspect mutatis mutandis.

Some examples of the disclosure provide for a low profile of the embolic protection device within the aorta which allows sheaths, catheters, or wires used in endovascular procedures on the heart to pass thanks to the tether.

Some examples of the disclosure also provide for avoiding of anchors, arms, bows extending from the device etc. that may cause tissue damage/cause debris to be scraped off and washed away.

Some examples of the disclosure avoid additional portions of the embolic protection device being in tissue contact with the aorta's or side vessels' inner wall, in particular adjacent or in the vicinity of ostia in the aortic arch.

The term "sustain" as used herein means one of support, aid, assist, keep up, uphold or the like. Sustaining a tissue apposition of a device according to the present disclosure may be provided by a push force or a pull force supporting, aiding or assisting apposition, depending on the specific embodiment.

The term "tether" as used herein shall not be confused with a safety tether, which is a simple safety line for allowing retrieval of an embolic protection device if needed. A tether as used herein is a line allowing controlled tensioning of an entire embolic protection device or selected portions thereof. Traction is applied proximally to the tether for the providing the tensioning of the device to an inner vessel. The tether is distally connected or attached to the embolic protection device such that the traction supports anchoring of the device against the inner vessel wall. In this manner a fluid flow at the periphery of the device is controllable and can be totally stopped by the degree of traction on the tether such that blood only passes a blood permeable unit of the device. As used herein, the term "tether" or "strand" refers to any elongated structure, e.g., cords, fibers, yams, filaments, cables, and threads, fabricated from any non-degradable material, e.g., polycarbonate, polytetrafluorothylene (PTFE), expanded polytetrafluorothylene (ePTFE), polyvinylidene fluoride, (PVDF), polypropylene, porous urethane, Nitinol, fluropolymers (Teflon®), cobalt chromium alloys (CoCr), and para-aramid (Kevlar®), or textile, e.g., nylon, polyester (Dacron®), or silk.

The device including the inventive improvement of embodiments, includes a collapsible embolic protection device devised for temporary transvascular delivery to an aortic arch of a patient, the device having a protection unit including a selectively permeable material or unit adapted to prevent embolic material from passage with a blood flow into a plurality of aortic side branch vessels at the aortic arch, wherein the protection unit is permanently or releasably (for assembly prior to introduction into the body) attached to a transvascular delivery unit at a connection point or region, or an attachment point, provided at the selectively permeable unit, and a first support member for the protection unit that is at least partly arranged at a periphery of the selectively permeable unit. In an expanded state of the device, the connection point is enclosed by the first support member or integral therewith, wherein the transvascular delivery unit is connected off-center to the protection unit at the connection point. In some embodiments, the connection point or region, or attachment point, is enclosed by the first support member.

The connection point may be provided at the selectively permeable unit or at the first support member.

The connection point may be provided on a surface of the selectively permeable unit devised to be oriented towards the aortic side branch vessels from inside the aortic arch and at a distance from the ostia regions when the protection unit is positioned in the aortic arch.

In some embodiments, the selectively permeable unit includes a first portion devised to extend in a first direction towards a descending aorta of the aortic arch from the connection point, and a second portion devised to extend in a second direction, opposite to the first direction, towards an ascending aorta of the aortic arch from the connection point, when the protection unit is positioned in the aortic arch, in the expanded state.

In some embodiments, the selectively permeable unit is arranged to asymmetrically extend from the connection point in a first direction towards a descending aorta of the aortic arch and in a second direction towards an ascending aorta of the aortic arch, when the protection unit is positioned in the aortic arch, in the expanded state.

The term "collapsible" used in the context of the present application means that a dimension of a device is reducible to a lesser dimension such that it is arrangeable in a tubular delivery unit, such as a catheter. A collapsible unit is expandable when released or pushed out of the delivery unit. Expandable includes self expandable, e.g. by a shape memory effect and/or resilient elasticity. A collapsible unit is the re-collapsible for withdrawal into the delivery unit and out of the patient.

It should be emphasized that the term "including/having" when used in this disclosure is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present disclosure, reference being made to the accompanying drawings, in which

FIGS. 18a-e are schematic illustrations of a catheter device according to embodiments of the invention;

FIGS. 19a-b are schematic illustrations of a catheter device according to embodiments of the invention;

DESCRIPTION OF THE PREFERRED EMBODIMENTS

Figure 1:
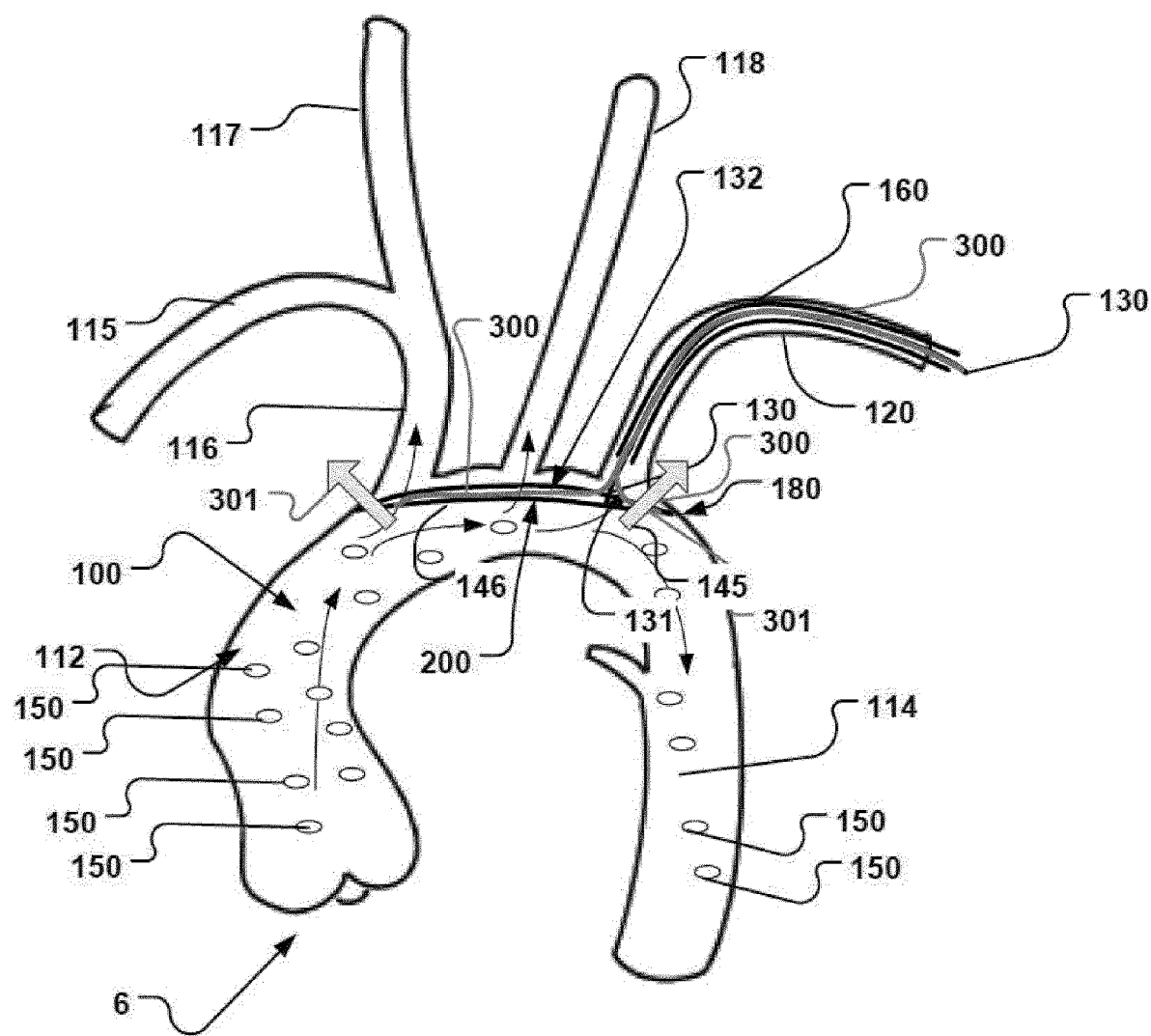
FIG. 1 is a schematic illustration of a protective device attached to a transvascular delivery unit in its expanded configuration deployed in an aortic arch, the device including a tether.

Specific examples will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 shows a schematic illustration of an aortic arch 100 and a plurality of side branch vessels, including a third side branch vessel 116, a second side branch vessel 118, and a first side branch vessel 120. The aortic valve 6 is illustrated in some of the Figs. Normally, three branches of the aorta split off from the trunk of the aortic arch 100 in three separate ostia. The third side branch vessel 116 is called the brachiocephalic artery, the second side branch vessel 118 is called the left common carotid artery, and the first side branch vessel 120 is called the left subclavian artery. The side branch vessels usually split from the aortic arch as three separate arterial trunks, arising from different positions on the aortic arch 100. The brachiocephalic artery 116 is the largest diameter branch of the aortic arch and normally gives rise to a bifurcation from which extend the right subclavian artery 115, leading blood e.g. to the right arm, and the right common carotid artery 117 conveying arterial blood towards the neck and head. The left common carotid artery 118 usually branches directly from the aortic arch 100. The common carotid arteries 117, 118 then branch into the external and internal carotid arteries that supply blood to the neck and head regions. The left and right subclavian arteries 120, 115 ultimately provide the arterial path for blood destined for the vertebral arteries, the internal thoracic arteries, and other vessels that provide oxygenated blood to the thoracic wall, spinal cord, and parts of the upper arm, neck, meninges, and the brain.

Figure 2:
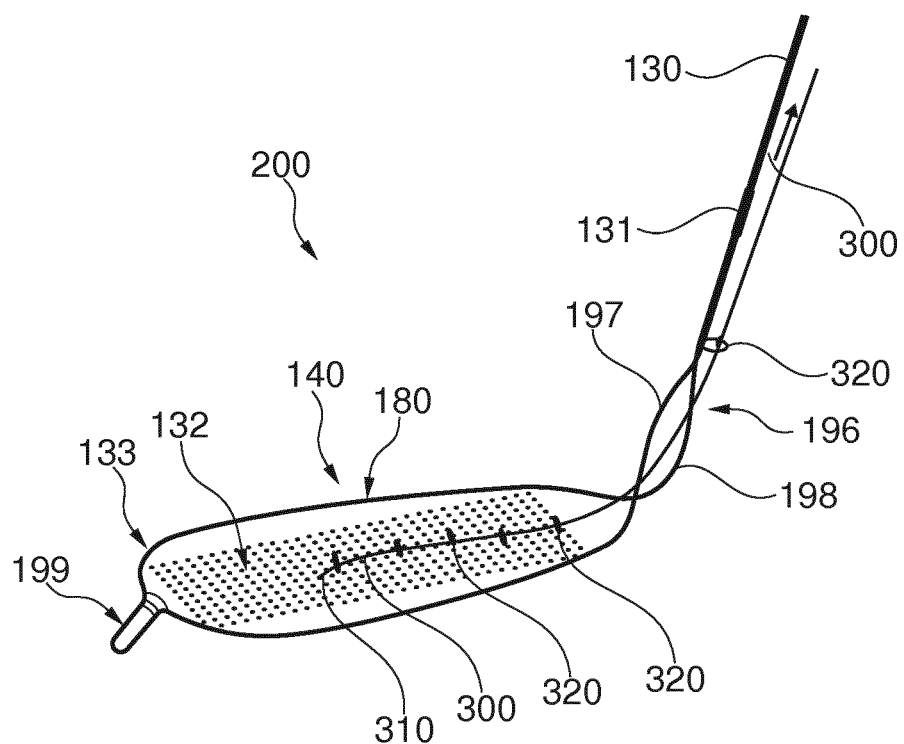
FIG. 2 is a perspective view illustrating an embolic protection device with a tether.
Figure 3:
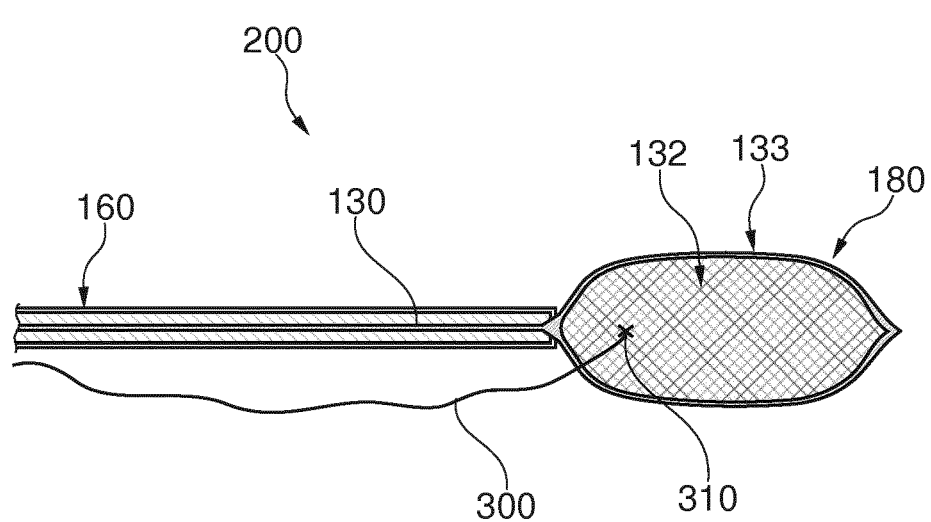
FIG. 3 is a planar view from above illustrating an embolic protection device with a tether.

FIG. 2 is a perspective view of an embolic protection device having a support member 133 of wire. Two branches of the wire cross each other at a crossing 196 towards the delivery unit 130. The wires are joined at attachment point 131, e.g. by clamping, welding, gluing.

The collapsible embolic protection device 200 is provided that is devised for temporary transvascular delivery to an aortic arch 100 of a patient, and temporary positioning in or across the aortic arch 100. Several examples of the device are described below. The devices have a collapsible protection unit 140 for preventing embolic material 150 from entering into at least one of the side branch vessels 116, 118, 120 of the aortic arch 100 in an expanded state thereof when suitably positioned in the aortic arch 100. Preferably at least the left and right carotid arteries 118, 117 are protected from embolic material 150 present in the aortic arch 100. All of the side branch vessels 116, 118, 120 may be covered.

The example of the embolic protection device 200 further includes a first support member 133 for the protection unit 140 that is at least partly arranged at a periphery 180 of the selectively permeable unit 132. The selectively permeable unit 132 is permeable for blood but impermeable for embolic material. The selectively permeable unit 132 is connected or attached to the first support member 133 by in a suitable manner. Alternatively, the selectively permeable unit 132 may be integral with the first support member 133.

The protection unit 140 includes a selectively permeable material or unit 132 adapted to selectively prevent embolic material 150 from passage with a blood flow (symbolic arrows in FIG. 1) into the plurality of aortic side branch vessels 116, 118, 120 at the aortic arch 100. The blood flow into the side branch vessels is substantially not hindered when passing the embolic protective device 200. The protection unit 140 is permanently connected to or attached to a transvascular delivery unit 130 at a connection point or region, or an attachment point 131 provided at the selectively permeable unit 132. The connection point or region may for instance be provided when the protection unit is integral with a support element thereof, and not attached thereto, but transiting from the transvascular delivery unit 130 to the protection unit 140, e.g. at a support member of the protection unit 140.

Depending on the characteristics of the selectively permeable unit 132, embolic material may be temporary trapped in the selectively permeable unit 132. The selectively permeable unit 132 may include a filter material. Alternatively, or in addition, the selectively permeable unit 132 may include or be made of a porous material. In any example of the devices of the disclosure, the selectively permeable unit 132 material can include braided, woven, or clustered material. In certain aspects, the selectively permeable unit 132 material can include laminated mesh. For example, the mesh can include polymeric film, e.g., perforated polymeric film. Alternatively, or in addition, the selectively permeable unit 132 may have characteristics that the embolic material glides or slides along a surface thereof oriented away from the ostia, thus deflecting embolic debris past the side branch vessels. In any examples of the devices of the disclosure, the protection unit 140 and/or the permeable unit 132 can include Drawn Filled Tubing, e.g., including an outer layer of Nitinol and/or a core that includes tantalum and/or platinum.

The first support member 133 is shaped to apposition to tissue of a vessel wall portion of the aortic arch 100. The first support member 133 is formed to encircle the plurality of ostia of the aortic side branch vessels 116, 118, 120 inside the aortic arch 100, and at a distance to the ostia. In this manner the selectively permeable unit 132 is arranged to separate a first fluid volume of the aortic side branch vessels 116, 118, 120 from a second fluid volume in the aortic arch 100 when the protection unit 140 is positioned in the aortic arch 100, as illustrated in FIG. 1. A blood flow occurs from the second fluid volume in the aortic arch 100 to the first fluid volume of the aortic side branch through the selectively permeable unit 132 preventing embolic particles of selected size to pass.

The embolic protection device is usually delivered transvascularly through a catheter 160 to the aortic arch. Delivery may be made through different vessels, other than those specifically illustrated as an example in the Figs.

According to one aspect of the disclosure, the collapsible, transluminally deliverable embolic protection device 200 for temporarily positioning in the aortic arch is connectable or fixedly connected to the transluminal delivery unit 130 extending proximally from a connection point 131. The device 200 has the first support member in form of a frame with the periphery 180, and the blood permeable unit 132 within the periphery 180 for preventing embolic particles 150 from passing therethrough into side vessels of the aortic arch 100 to the brain of a patient. The device further includes at least one tissue apposition sustaining unit, which is not a delivery shaft of the device. The tissue apposition sustaining unit is provided for application of a force offset to the connection point at the device.

A tissue apposition sustaining unit provides for supporting a tissue apposition of the device 200 to the inner wall of the aortic arch.

Offset to the connection point may for instance be at the periphery 180. It may also be adjacent the periphery 180. It may also be centrally of the blood permeable unit 132 within the periphery 180.

The force, also called stabilization force, is applied or directed towards an inner wall of the aortic arch 100 when the device is positioned in the aortic arch. The force is in an example illustrated in the Figs. by the arrow 301.

In this manner tissue apposition of the periphery 180 to an inner wall of the aortic arch 100 is supported by the force as illustrated by arrow 301. The aortic arch provides a counterforce as it has limited flexibility and elasticity. This equilibrium of force and counterforce entrails improved sealing of the periphery 180. It may also provide for limited motion of the aortic arch at the embolic protection device as the device is locked more or less into place. However, movement of the aortic arch may still be present and compensated as described herein, for instance to prevent the so-called windsucker effect disadvantages.

For instance, a tractive force such applied may pull a periphery of the device against the inner wall. The force supports the aforementioned locking the device in place upon implantation.

The embolic protection device 200 can thus be reliably placed across the apex of the aorta in order to prevent emboli from flowing into the carotid arteries. The inventive solution is not iatrogenic, as it prevents creation of debris from e.g. ostia of side vessels. Iatrogenic relates to an adverse condition in a patient resulting from treatment by a physician or surgeon. Arms, anchors, delivery shafts, bows, etc. of inferior embolic protection devices, for instance extending into the side vessels, risking scraping off of plaque from the inner vessel wall or ostia, are not needed and can be avoided thanks to the present disclosure.

The embolic protection device 200 may be a deflector for deflecting embolic particles. Alternatively, or in addition, it may in examples be a filter for catching embolic particles.

Figure 10:
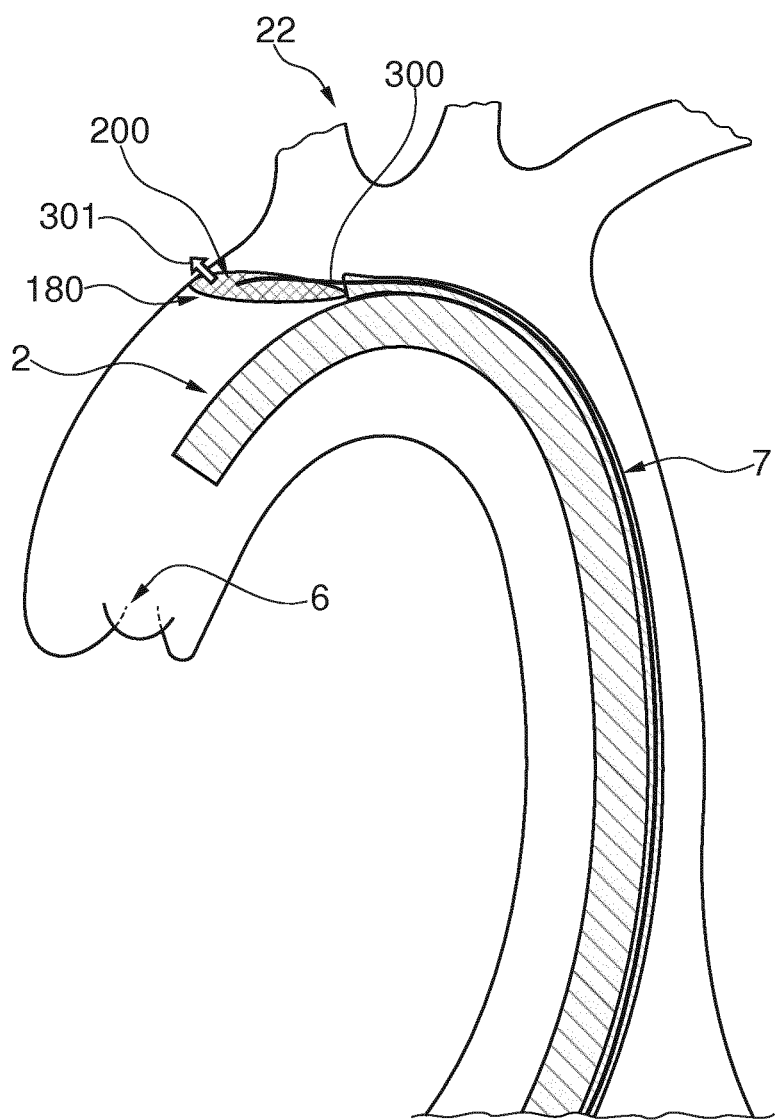
FIG. 10 is a schematic view illustrating a catheter delivered via a femoral approach with a side channel and an embolic protection device with a tether.
Figure 11:
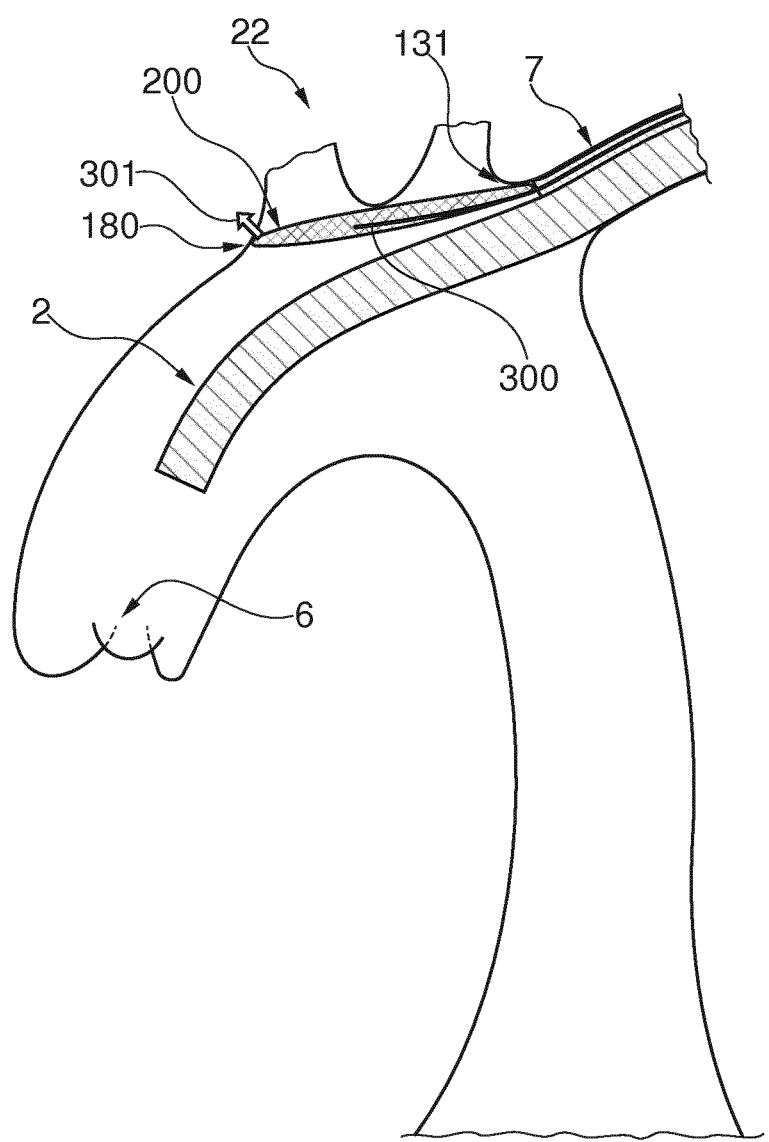
FIG. 11 is schematic view illustrating a catheter with a side channel and an embolic protection device with a hinge and a tether, delivered via a side vessel.

The device may in examples be deliverable via a side channel 7 of a catheter 2, e.g. via a femoral approach. Such as side channel catheter 2 is described in PCT/EP2012/0058384, which was published after the priority date of the present application as WO2012152761, and which is incorporated herein by reference in its entirety for all purposes. The catheter may further be improved by multiple side channels, wherein one side channel 7 is provided for conveying the embolic protection device 200 to the aortic arch 100. Tethers 300 may run in the same channel or other channels of the catheter as the embolic protection device 200 and delivery unit 130. A pigtail catheter may be provided in such an auxiliary side channel. The pigtail catheter may be used to further stabilize the catheter in a femoral delivery approach, supporting the catheter 2 against the annulus of the aortic valve and inner wall of the aortic arch, such as described in WO 2012/094195 A1, which is incorporated herein by reference in its entirety for all purposes, see in particular FIGS. 10A and 10B of WO 2012/094195 A1 as well as related description passages in WO 2012/094195 A1.

The device 200 may in examples be deliverable via a side vessel, such as described in WO 2010/026240 A1.

The device may in examples be deliverable through the wall of the aorta 100, e.g. in a so called direct aorta approach.

The aforementioned force 301 may include or be a tractive force depending on the type of apposition supporting unit. The apposition sustaining/supporting unit may then be an active traction unit that has for instance at least one operable tether 300 distally connected at the location offset the connection point. The distal connection location of the tether may be located at the frame, periphery and/or blood permeable unit, of the embolic protection device for providing the tractive force. The tether has one or more distal end(s). The distal end is for instance connected to the periphery of the embolic protection device. The tether's distal end(s) may be connected to the blood permeable unit, such as a filter or deflector membrane. The membrane may be moved by the traction, e.g. if the membrane is flexible and/or elastic.

Tether(s), or more precisely, tetherline(s) are provided to control a sealing degree of the periphery. Tether(s) are provided for direction of apposition towards aortic tissue/cerebral arteries. The tether may provide active traction by a pull action on the tether communicated to the embolic protection device to which it is distally connected.

The tether may be arranged longitudinally movable relative the delivery unit 130. In this manner, the device 200 is positionable in the aortic arch so that the delivery device may be locked in a "delivered" position, by the delivery unit 130, e.g. at its proximal end at or outside a port of an introducer. The tether 300 may then still be movable and improve sealing as described herein.

Tether(s) 300 may be multifilament(s), which provides for a particularly flexible solution advantageous for narrow lumen navigation.

A tether 300 may extend straight across the blood permeable unit to the forward end of the device. Thus the middle line may be pulled up and the periphery is tensioned against the inner wall. The tether provides for a lifting force to the forward end. In case the tether is guided at the middle line, e.g. threaded through eyelets, it may provide a progressive lifting force distributed along the device. See for instance FIGS. 2, 6, 7 and 8.

The at least one tether 300 may be longitudinally elastic, i.e. it is longitudinally stretchable and resiliently return to a non-stretched longitudinal extension. The tether may be elastic along its entire length. The tether may include one or more elastic portions or elastic elements. The elastic portion may be a helical wound portion of the tether acting as a spring. The elastic portion may be a tubular braid of a double helically wound strands. The elastic portion may be made of an elastic material, preferably biocompatible, like rubber. In this manner the tractive force is variable. This may be advantageous for preventing rupture of the tether line as a non-linear extension may be "felt" by an operator. This variable traction force may also be advantageous if the tether is tension, applying a desired traction for improving sealing of the embolic protection device. The tether may be locked at its proximal end in this position, e.g. extending out of an introducer port. The elasticity may provide for compensating physiological movements of the aortic arch relative a proximal end of the device and/or tether while maintaining the tissue apposition. The applied force is provided within a certain range suitable to maintain the improved peripheral sealing while the aortic arch moves due to the beating heart and blood pulse waves.

The blood permeable unit 132 may have at least one guiding unit 320, such as an eyelet, a tubular bent element, a roller, an open pocket fabric portion, etc. The guiding unit may receive the tether proximally its distal end where it is attached to the device, such as at the blood permeable unit, flange, or periphery. The guiding units, such as eyelet(s) etc. provide for locally controllable apposition at the device. The traction force may be distributed to different areas of the device.

The device may have an attachment point where a distal end of the tether is connected to the device and a tractive force is transmissible via the attachment point to the device towards the periphery. Optionally one or more radiopaque fiducial markers may be provided at the device. A fiducial marker may be provided at the attachment point. Such radiopaque elements can be affixed to, or incorporated into the intra-vascular device, e.g., affixed to the frame 133, selectively permeable unit, yoke, skeleton or other radiating support members, the tether, eyelet, etc. to provide identification of the orientation of the device 200 when inside the body of the patient. The radiopaque element can be a bead or clamp. In the case of a clamp, the element can be crimped onto the device 200. Radiopaque material can be incorporated into wire or tether. Portions of the frame, yoke or permeable unit 132 can be constructed out of DFT wire. Such wire can contain, e.g., a core of tantalum and/or platinum and an outer material of, e.g., Nitinol. Radiopaque elements or fiducial markers provide for advantageous X-ray visibility and navigation, position feedback and control of the device.

In some examples, the tether is proximally extending through an ostium into a selected side vessel such that the tractive force centers the device in relation to the ostium. When pulling the tetherline 300, it pulls the device at its periphery against the inner wall of the aorta for locking the device in place. In this manner the device is self aligning in relation to the ostium of the selected side vessel thanks to the tether. The skilled person may provide suitable guiding units for the tether when reading this disclosure to obtain this function.

The device may include multiple tethers distally attached along the periphery. Alternatively, or in addition, a single proximal tetherline may separate distally into a plurality of (sub)tetherlines. For instance, a tether may be branched in the form of a Y. A single tether to be operated proximally may then distribute a tractive force distally via its two distal end points to the embolic protection device.

Figure 8:
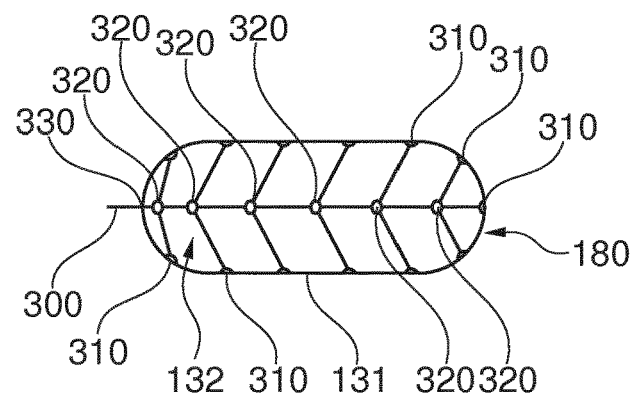
FIG. 8 is a planar view from above illustrating an embolic protection device with multiple tethers
Figure 9A:
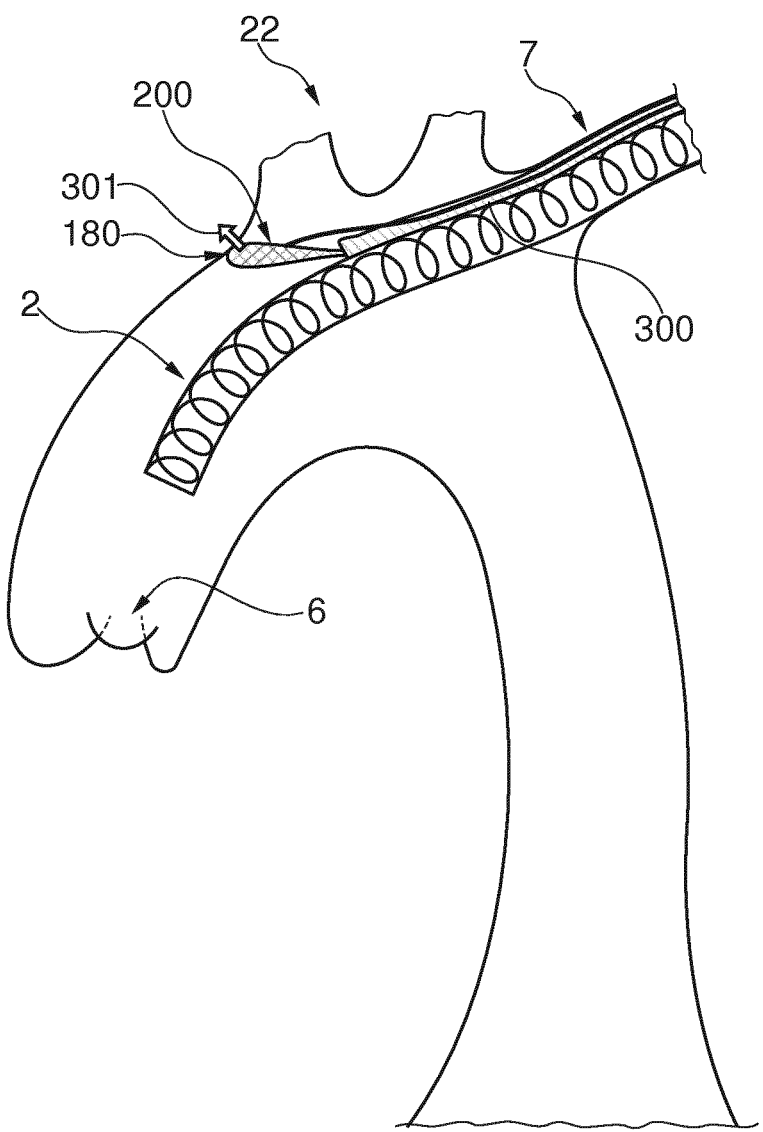
FIGS. 9A and 9B are schematic views illustrating a catheter with a side channel and an embolic protection device with a tether, delivered via a side vessel.
Figure 9B:
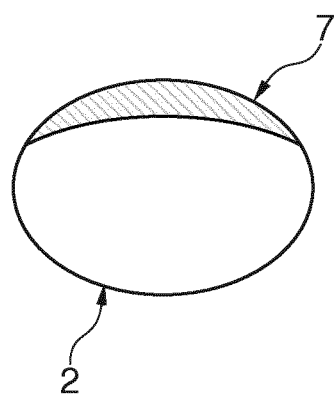

An example with a plurality of endpoints is shown in FIG. 8. Multiple tethers may be used or combined with tethers having multiple distal ends. The multiple tethers may be collected proximally at the device, e.g. at a base 330 (FIGS. 7, 8) thereof. In this manner, the device provides for a progressive force that is evenly distributed along the periphery of the device. The device may in this manner advantageously adapt to the inner shape of the aortic arch 100. The adaptation may even more enhanced by providing longitudinally elastic portions at the tether(s). For instance, the branched (sub)tetherlines may be provided of elastic material, while the main line is substantially non-elastic, but flexible.

Figure 4:
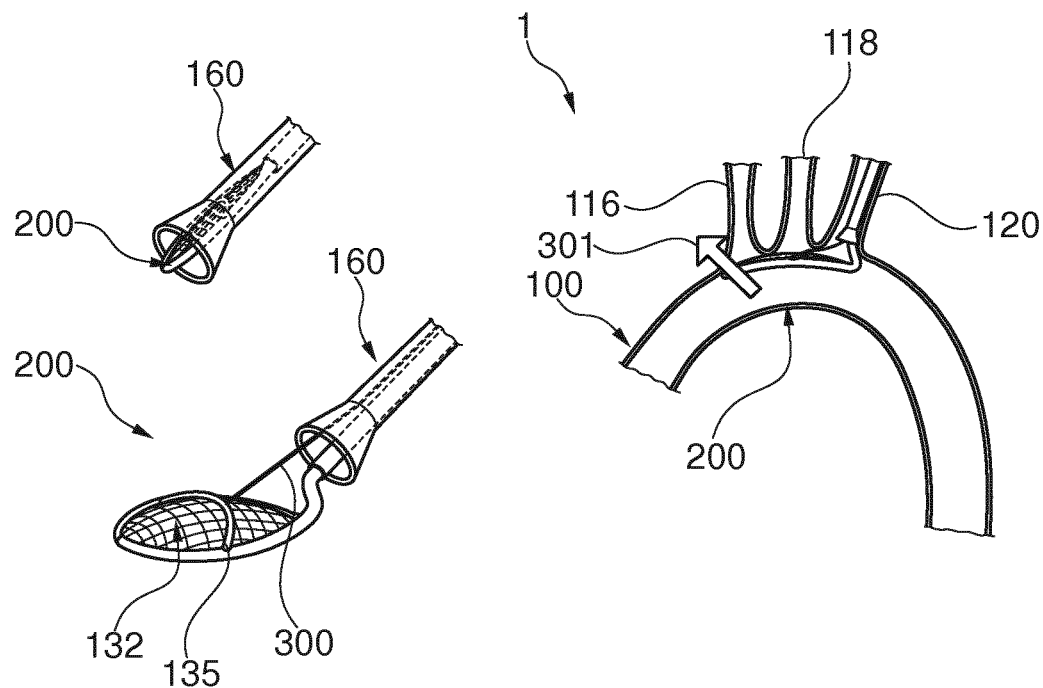
FIG. 4 is a schematic illustration showing an embolic protection device with a tether in a catheter, outside a catheter, and delivered in an aortic arch.
Figure 5:
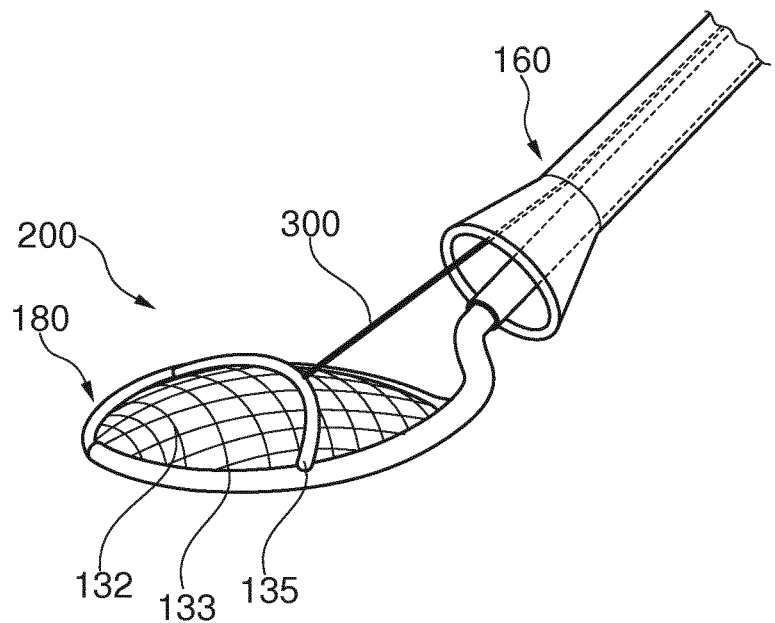
FIG. 5 is a perspective view showing the device of FIG. 4 enlarged and in more detail.
Figure 6:
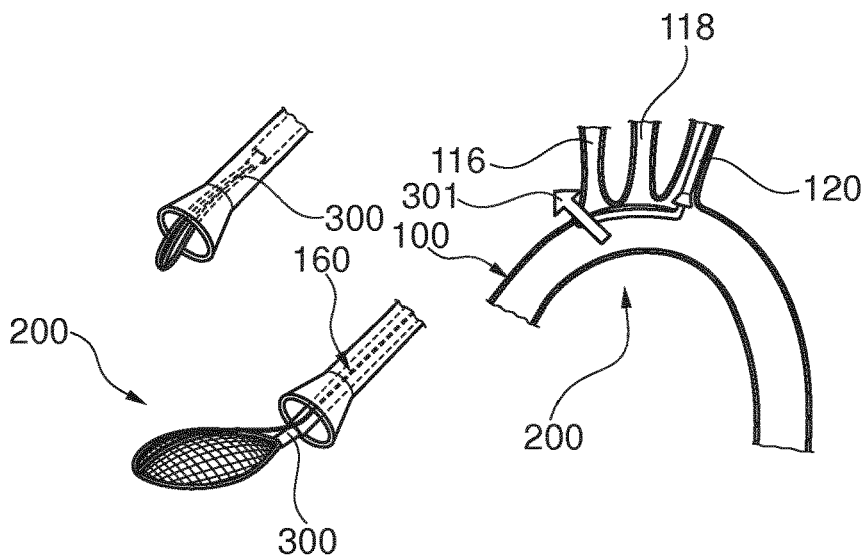
FIG. 6 is a schematic illustration showing an embolic protection device with a tether in a catheter, outside a catheter, and delivered in an aortic arch.
Figure 7:
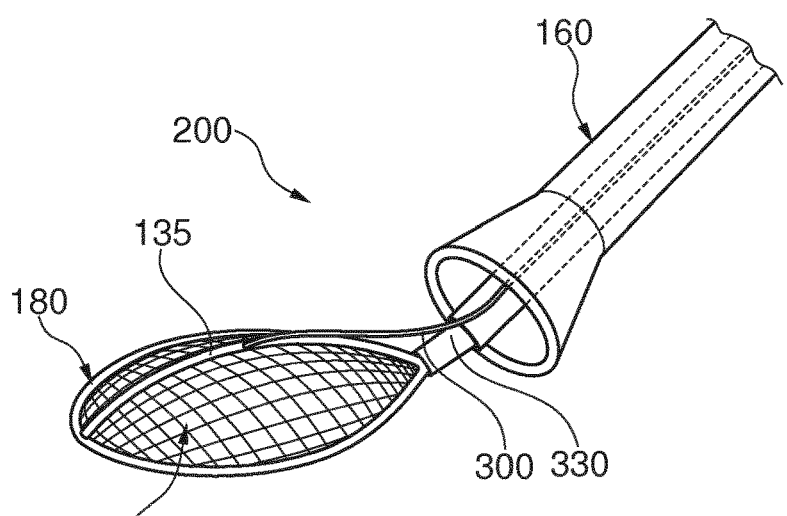
FIG. 7 is a perspective view showing the device of FIG. 6 enlarged and in more detail.

In some examples, the device may have an internal structure or an outer skeleton, such as at least one rib 135 extending between different, preferably opposite, joints at the periphery, wherein the tether is distally attached at the rib. The tether 300 may thus apply a tractive force to the rib 135, which in turn transfers the force to the periphery 180 of the device 200 towards the aortic inner wall tissue. The rib 135 may be a beam or yoke. It may be arranged longitudinal (FIG. 6, 7) or transversal (FIG. 4, 5) in relation to the expanded device's 200 longitudinal axis.

There may be a plurality of such ribs 135 in a device.

For example, this internal structure, e.g., a rib 135, can permit an operator to control the orientation of the device within the aortic arch and allow the operator to push, press or draw the device against certain features of the aortic arch, e.g., to press the device onto the aortic arch wall at a distance from and over the ostia of one or more of the side vessels. An outer skeleton may be connected to the internal structure. The outer skeleton may be the frame 133 and can provide additional structural support for the device and can facilitate the creation of a seal between the selectively permeable unit 132 of the device and a blood vessel wall. Alternatively, the permeable unit 132 itself may create a seal against the blood vessel wall by extending beyond the perimeter of the frame 133.

The device 200 may be capable of collapse along its longitudinal axis for ease of delivery to the treatment site. The device 200 may further be compatible with common delivery methods used in interventional cardiology, e.g., TAVI procedures. The device may be integrated into a delivery system, such as including a side channel catheter. Upon retrieval the device 200 may be retracted in orientation substantially similar to the original deployment orientation.

Devices 200 having multiple petals or wings may have one or more ribs on one or more of the petals or wings to obtain a favourable force distribution.

For instance a petal or wing of the device may be arranged upstream in relation to the aortic blood flow. Alternatively, or in addition, the device 200 may have a petal or wing of the device may be arranged downstream in relation to the aortic blood flow. One or more, or each of the petals or wings may have tissue apposition sustaining unit(s), like tethers, pushers, springs as described herein. It may be sufficient to provide petals or wings arranged upstream in relation to the aortic blood flow with tissue apposition sustaining unit(s). Petals or wings arranged downstream may be sufficiently pushed against the aortic inner wall tissue by the pulsatile blood flow in the aorta passing along the blood permeable unit of the device. However, having tissue apposition sustaining unit(s) at petals or wings arranged in downstream direction from a connection point may advantageously be supported by such tissue apposition sustaining unit(s) during pressure changes in the aorta. The aortic pressure is lower during the diastolic phases and may tend to be more leaky than during systolic phases. The tissue apposition sustaining unit(s) may be dimensioned to be sufficient supportive during diastole, and thus be more advantageous (smaller, less mass) for insertion into the body than being dimensioned for systolic pressure support.

The tissue apposition sustaining unit(s) may limit movement of the blood permeable unit 132 caused by the pulsatile blood flow. For instance having a rib 135 may provide for this limited movement range. The rib(s) and/or tether(s) may limit movement of the blood permeable unit. Having connected a tether 300 to the device 200 may provide then for a progressive traction force and particularly improved sealing as forces on the periphery 180 caused by pulsatile pressure changes are evenly distributed during heartbeat's pulsatile flows.

The rib 135 may be a yoke extending proximally above the blood permeable unit 132. The yoke may preferably extend in a longitudinal direction of at least a portion of the device 200. The distal tether end(s) may be directly attached to the rib 135. The distal tether end(s) may be guided by guiding units(s) at the rib to the to periphery 180, providing an advantageous distribution of tractive force.

The device 200 may include multiple tethers, or a single tether splitting distally into multiple strands. In an example two tethers or strands are distally attached to the periphery in a Y-shape from a base of the device (see FIG. 8).

The device 200 may include at least one eyelet, wherein one or more of the tethers are threaded through at least one eyelet. An eyelet may preferably be provided at a pivot point and/or at a base 330 of the device 200.

The blood permeable unit may be flexible. It is for example a flat membrane with defined porosity or holes. The porosity or holes may be part of or included in a fine wire netting or mesh, or a perforated film. Such as a mesh or sheet having holes or porosity of 50-950 microns (e.g., 50, 60, 70, 80, 85, 90, 100, 120, 135, 150, 250, 350, 450, 550, 650, 750, 850, 950, or more microns. Perforated film may be perforated prior to the inclusion with the device. The film may also be perforated post inclusion with the device, e.g., by laser drilling or electric sparks. In embodiments where a perforated film is present, the pores can have constant or varied pore patterns, constant or varied pore densities, and/or constant or varied pore sizes. The blood permeable unit 132 may be braided, weaved, clustered, knitted, or knotted. The blood permeable unit 132 may be of a non-degradable material, e.g., polycarbonate, polytetrafluorothylene (PTFE), expanded polytetrafluorothylene (ePTFE), polyvinylidene fluoride, (PVDF), polypropylene, porous urethane, Nitinol, fluropolymers (Teflon®), cobalt chromium alloys (CoCr), and para-aramid (Kevlar®), or textile, e.g., nylon, polyester (Dacron®), or silk. The blood permeable unit 132 may be a combination of materials, e.g., the combination of DFT and Nitinol wires. The blood permeable unit 132 may also be coated with an anti-thrombogenic agent to prevent a thrombogenic reaction. The size of the device 200 may be pre-sized and pre-formed to accommodate various patient groups, e.g., children or adults, or a particular aortic anatomy.

A tether may be distally attached to the membrane. A traction force thus applied may raise the membrane out of a plane of the membrane, such that for instance to a volcano shape, including the attachment location of the tether to the membrane at the to thereof. The volcano shape may be advantageously increasing the efficiency of the device. The top of the volcano shape may be arranged to extend into an ostium, into a portion of a side vessel. Trapping of particles may thus be improved by the interior funnel shape of the volcano into which blood flows. Increased filter efficiency will be the result.

The traction unit may include a passive traction unit. The passive traction unit is not operated by an operator, but provides automatically for the improved sealing. The passive traction unit may be a spring. It may have a shape memory element for instance activated by body temperature, such as a portion of the frame, for providing the tractive force relative a delivery portion or device. For instance the device may include "winglets" extending from the periphery of the device which have a shape memory. Another example is shape memory springs that are activated to tension tethers, e.g. from a base of the device. A portion of a tether may be provided as a shape memory portion. Such tether may be delivered in an elongate shape and then change to a memory induced shape, shortening the tether to provide the tensile force. The memory induced shape may be a helical coil shape additionally allowing for elasticity of the memory activated tether, particularly advantageous for pressure and/or movement compensations.

Figures 14, 15:
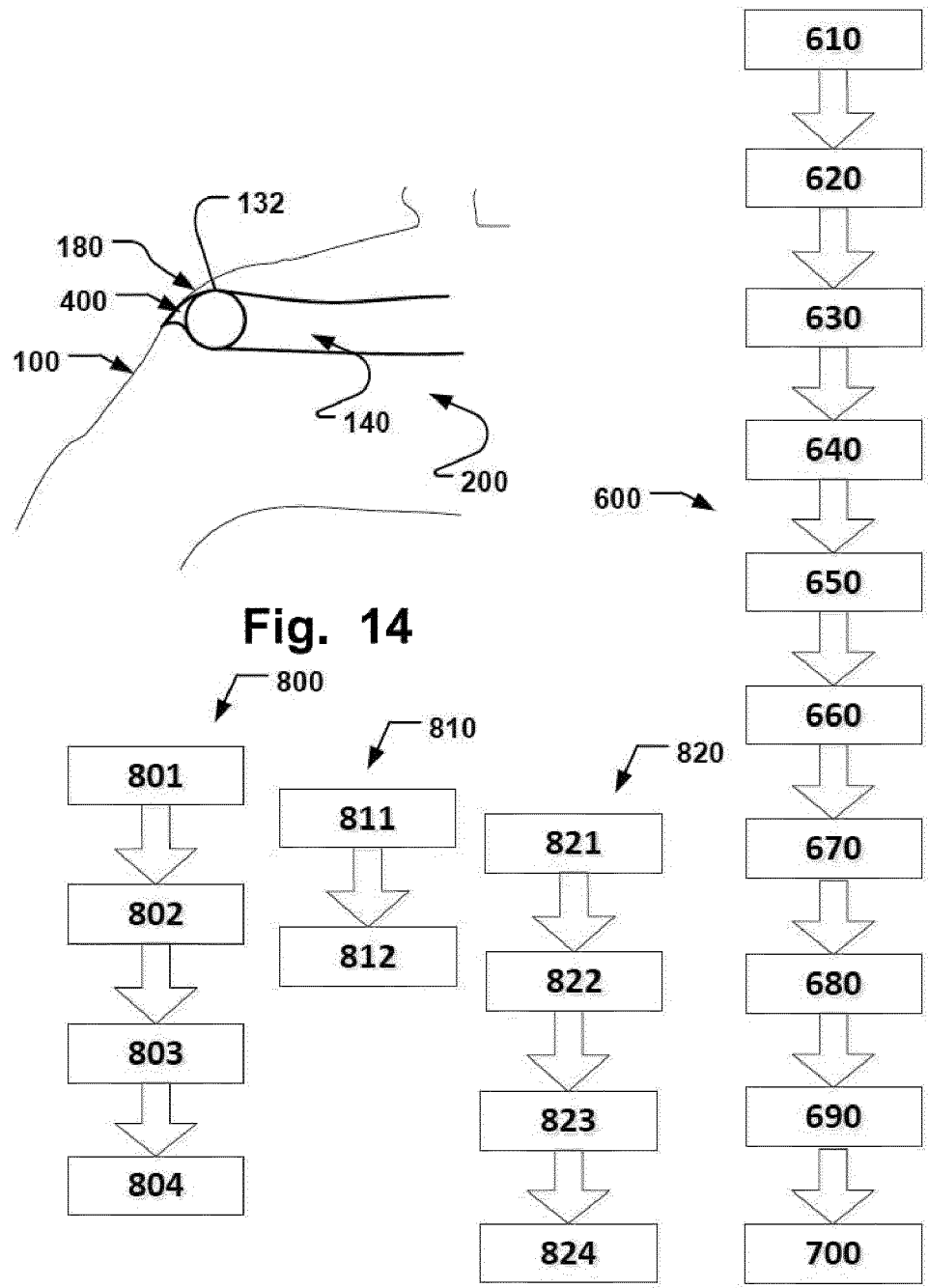
FIG. 14 is a schematic view illustrating an embolic protection device with a flange unit 400.
FIG. 15 is a flowchart illustrating a method 600.
Figure 16A:
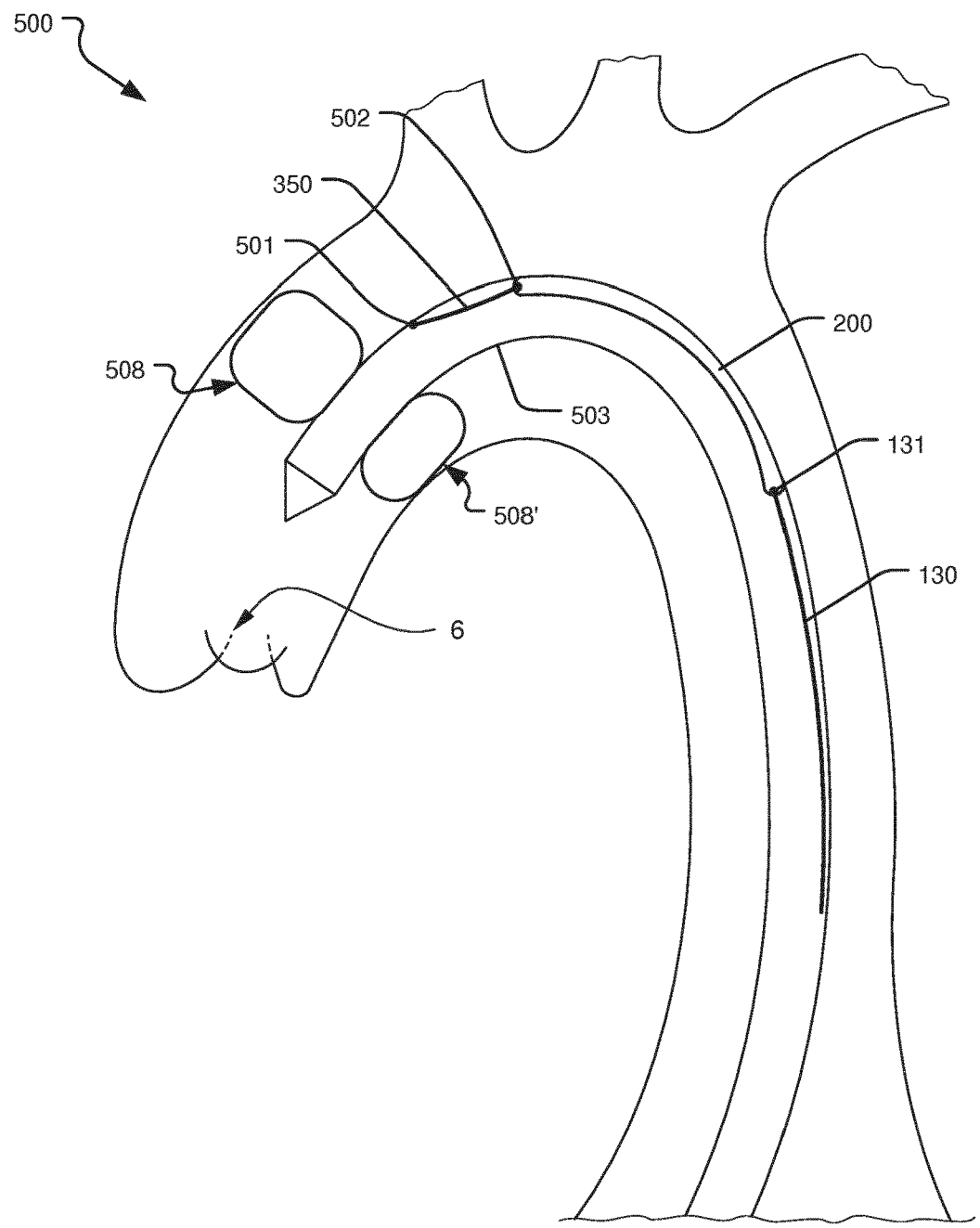
FIGS. 16a-c are schematic illustrations of a catheter device according to embodiments of the invention.
Figure 16B:
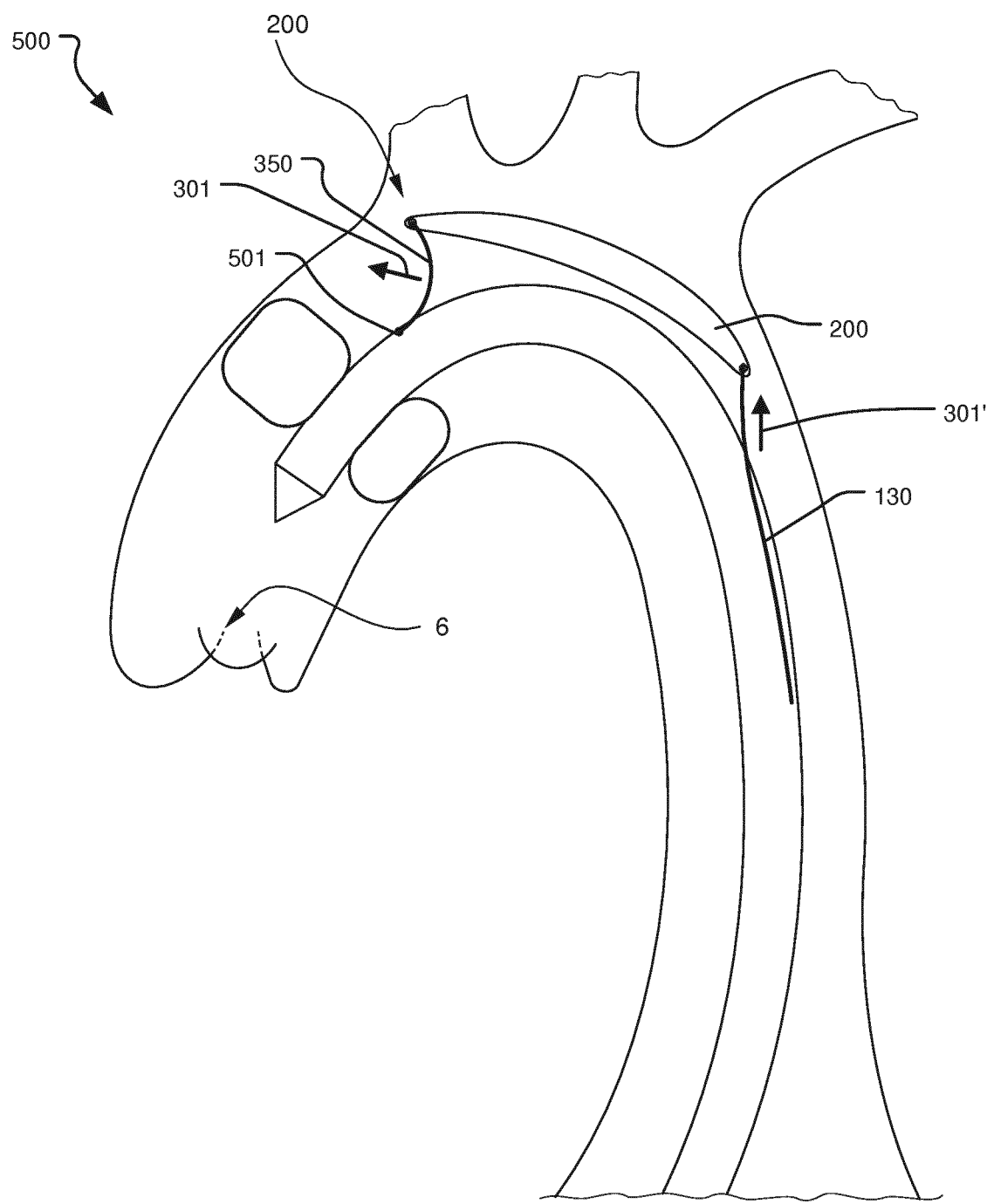
Figure 16C:
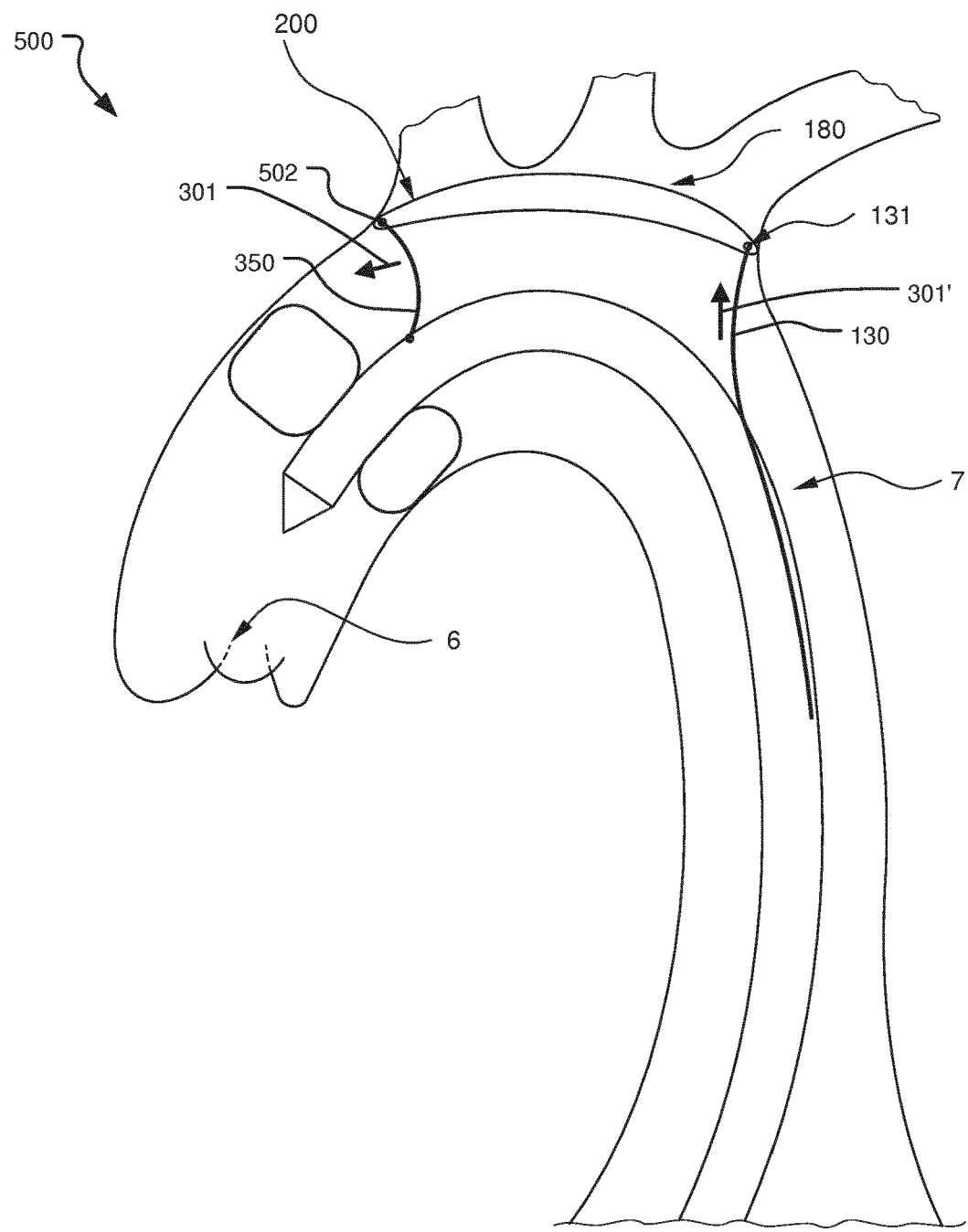

The device may have a flange unit 400 extending radially outward from the periphery 180 of the device 200, e.g. from the frame 132, see FIG. 14. The flange unit may be angled in relation to a plane of the blood permeable unit for a pre-tension against which the tractive force is provided. The flange unit may provide for further improved sealing as sealing is supported by the blood pressure in the aorta. The flange unit 400 may be made of a fabric. The fabric may be woven. The fabric may be woven from PTFE threads providing for advantageous sealing and biocompatibility. The fabric may be arranged as a collar around the frame of the device. The collar may extend in a direction opposite to a filter membrane attached to the frame. The flange unit 400 provides for reducing or avoiding recesses at the periphery of the device towards the inner wall tissue. This is particularly advantageous as embolic particles may collect in such recesses. These collected particles may then be flushed into the side vessels when the device is removed. Avoiding particles collecting at the periphery reduces this potential issue.

Figure 12:
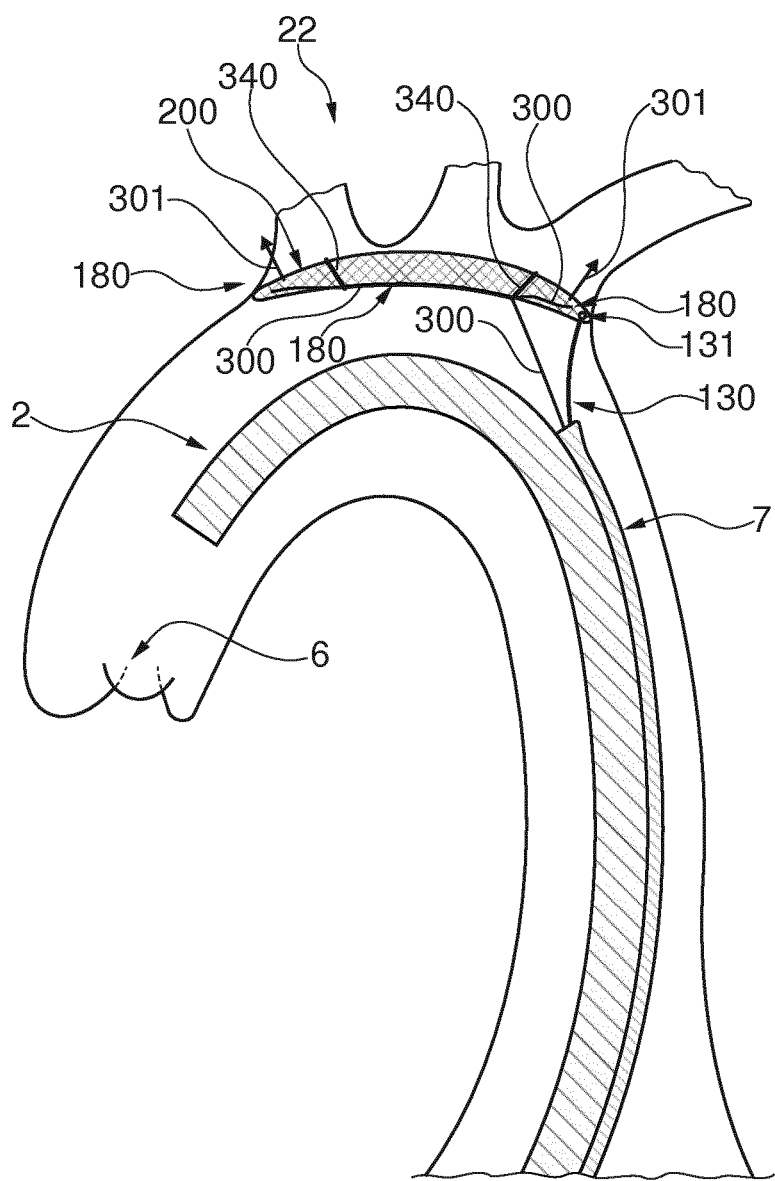
FIG. 12 is a schematic view illustrating a catheter delivered via a femoral approach with a side channel and an embolic protection device with multiple tethers.

FIG. 12 is a schematic view illustrating a catheter delivered via a femoral approach with a side channel and an embolic protection device with a tether; the device includes hinge portions 340 allowing for an upward movement conversion of the tractive force towards the aortic inner wall tissue, as shown in the FIG. A traction is thus converted into a pushing force.

Figure 13:
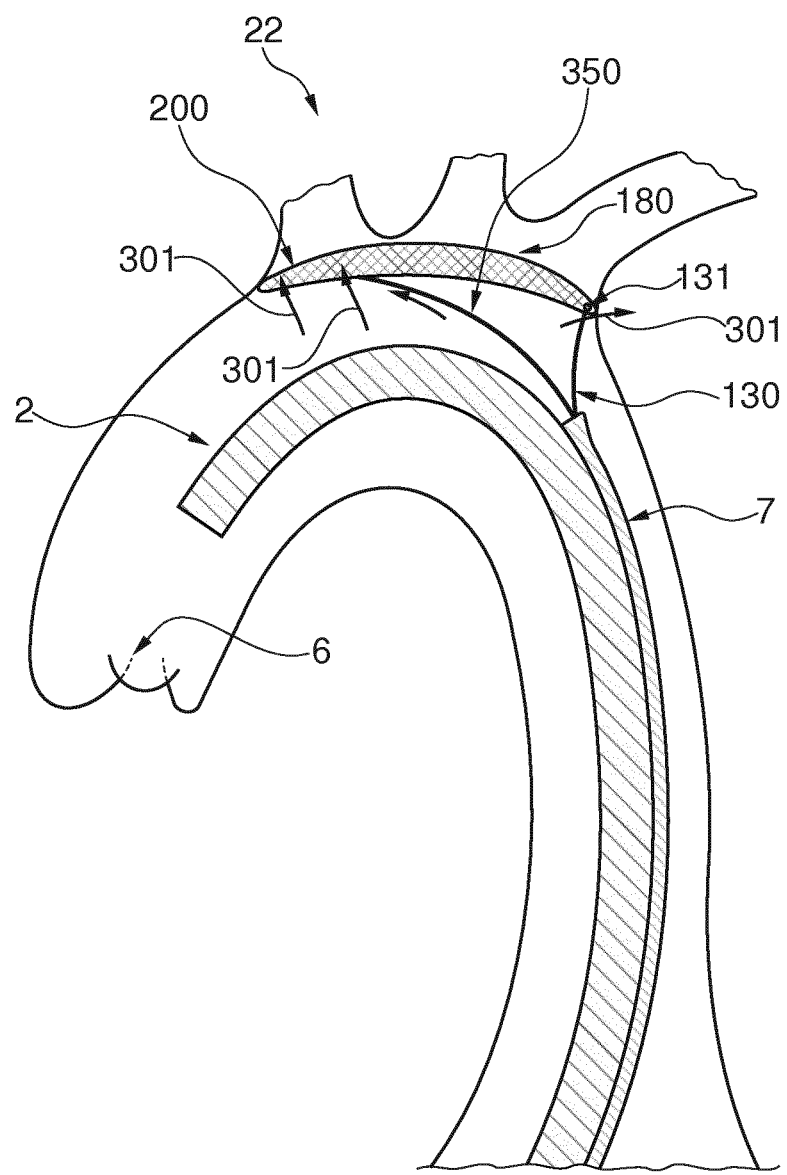
FIG. 13 is schematic view illustrating a catheter with a side channel and an embolic protection device with a pushing unit, delivered via a femoral approach.

The tissue apposition sustaining unit may include a pushing unit 350 (FIG. 13), and the force includes a pushing force, against the frame, periphery and/or blood permeable unit. The pushing unit provides the pushing force and presses the periphery to the inner wall.

The tissue apposition sustaining unit may include a magnetic element and the force includes a magnetic force.

The magnetic force my be provided as follows: the device 200 comprises a magnetic element of a first magnetic polarity. A second magnetic element may be arranged outside of the aortic arch. The second magnetic element has an opposite magnetic polarity than the first magnetic polarity. In this manner, the first and second magnetic elements attract each other. The device 200 will hence be drawn towards the aortic arch wall providing the force improving the sealing of the periphery 180. The skilled person will recognize suitable timing and locations to apply the second magnetic element. For instance, it may be arranged outside of the body in a suitable direction on the thorax of the patient after the embolic protection device is positioned in the aortic arch.

A repellent magnetic force may be obtained based on the same principle, but with first and second magnetic elements of identical polarity. The second magnetic element may for instance be part of or advanced through the catheter 7 or a side channel thereof when the device 200 is released and positioned from the side channel 7. In this manner, a force pushing the device against the inner aortic wall is provided.

Magnetic elements may be provided in addition to or alternatively to tethers, pushers, etc.

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labelled, for example with an appropriate date through which the article is expected to remain in fully functional condition. The components can be packaged individually or together.

Various devices described herein can be packaged together in a kit for convenience. The kit can further include, for example, labelling with instruction for use and/or warnings, such as information specified for inclusion by the Food and Drug administration. Such labelling can be on the outside of the package and/or on separate paper within the package.

The device 200 may be used in a method of positioning an embolic protection device, such as a deflector and/or filter, in the aortic arch, is disclosed. The method includes transluminally delivering the embolic protection device to the aortic arch, the device connected to a transluminal delivery unit 130 extending proximally from a connection point 131 of the device. Further the method includes positioning the device in the aortic arch. The positioning includes expanding a frame of the device and flattening a blood permeable unit in the aortic arch, and bringing a periphery of the device in apposition with an inner wall of the aortic arch to cover ostia of side vessels at least includes the carotid arteries. Thus positioned, the device is preventing embolic particles from passing therethrough into side vessels of the aorta to the brain of a patient.

In an example of a method 600, the device 200 is positioned in the aortic arch 100 by using a standard Seldinger technique and fluoroscopy with access through an introducer in the left radial artery. Once the collapsible protective device is delivered/released out of the catheter it expands and is placed to cover the left and right carotid arteries, letting through blood but not embolized particles. When the cardiovascular intervention or cardiac operation is over the device is retracted into the catheter again.

In the method 600 of preventing embolic material from entering side branch vessels with a blood flow from an aortic arch of a patient, a collapsible embolic protection device 200 is percutaneously introduced in a collapsed state into a peripheral blood vessel, as illustrated by step 610. This is schematically illustrated in FIG. 15. The collapsible embolic protection device 200 is transvascularly delivered in a collapsed state into the aortic arch 100 via the peripheral blood vessel and the first side branch vessel 120, as illustrated by step 620. For this purpose, the device 200 is collapsed into a delivery catheter 160 and introduced through the latter to the deployment site inside the aortic arch 100.

The device 200 is attached to a transvascular delivery unit 130, such as a pusher or wire, at an attachment point thereof. The embolic protection unit 200 of the collapsible embolic protection device is expanded in the aortic arch 100, which is illustrated by step 630.

The expanding may include asymmetrically expanding a first portion 145 of the protection unit and a second portion 146 of the protection unit from the attachment point 131 (see FIG. 1). The first portion 145 is expanded in a first direction towards the descending aorta 114 of the aortic arch 100. The second portion 146 is expanded in a second direction towards the ascending aorta 112 of the aortic arch 100. The asymmetric arrangement facilitates the positioning of the device 200 from the delivery vessel 120 in relation to the other side branch vessels 116, 118 to be protected. This method stage is illustrated by step 640.

The positioning the protection unit 200 in the aortic arch 100 includes appositioning a first support member 133 of the selectively permeable unit 132 of the protective unit 200 to tissue of a vessel wall portion of the aortic arch 100, as illustrated by step 650. The first support member 133 of the protection unit 200 is at least partly arranged at a periphery 180 of the selectively permeable unit 132 of the protection unit.

The method includes encircling a plurality of ostia of the aortic side branch vessels 116, 118, 120 in the aortic arch 100 with the first support member 133, and positioning the protective unit 200 at a distance to the ostia. This method stage is illustrated by step 660.

Thus, the protection unit 200 is positioned in the aortic arch 100 in the expanded state thereof, as illustrated in method step 670. Embolic material 150 is effectively prevented from passage with a blood flow into a plurality of aortic side branch vessels 116, 118, 120 at the aortic arch 100 by the selectively permeable material of the protection unit 200, see method step 680.

The method thus provides for concurrently separating a first fluid volume of the aortic side branch vessels from a second fluid volume in the aortic arch when the protection unit 200 is positioned in the aortic arch 100.

The method may include drawing the expanded protection unit 200 into a direction opposite a delivery direction, and thus tensioning and tightening against a vessel tissue portion of the aortic arch 100 encircling the ostia of the side branch vessels. This embodied method stage is illustrated by step 690.

Moreover, the method includes a step 700 of applying a force by at least one tissue apposition sustaining unit, not being a delivery shaft of the device, to the device. The force is applied offset to the connection point at the device, such as at the periphery. The force is directed towards an inner wall of the aortic arch when the device is positioned in the aortic arch. In this manner tissue apposition of the periphery to an inner wall of the aortic arch is supported by the force.

This method is less iatrogenic than known methods. It provides for further improved sealing of the periphery of an embolic protection device. It further prevents creation of debris from an ostium in the aortic arch, which might be an issue with some known embolic protection devices.

The supported apposition is improving apposition of the periphery to the inner wall of the aortic arch, such that the improved apposition provides for improved sealing of the periphery against the inner wall.

The force may be applied in a substantially proximal direction relative the device for the improved sealing.

Applying the force may include applying a tractive force by a traction unit. The tractive force may include pulling a periphery of the device against the inner wall for locking the device in place in the aortic arch. The tractive force may be applied by at least one tether distally connected to the frame, periphery and/or blood permeable unit for providing the tractive force.

The device may be delivered to the aortic arch via one of the side vessels, such as the brachiocephalic artery from the right subclavian artery, the left carotid artery, or the left subclavian artery. It may be delivered to the aortic arch via the descending aorta such as in a femoral approach, e.g. in a side channel of a main catheter. It may be delivered to the aortic arch through the wall of the ascending aorta, which is an approach called "direct aorta" approach.

The device 200 may be used in a method 800 of preventing emboli flowing in the aortic arch from entering side branch vessels thereof, is provided. The method includes a step 801 advancing an embolic protection to the aortic arch; and a step 802 manipulating the protection device such that it covers the ostia of each of the side branch vessels. The method further includes a step 803 applying a force to the protection device for improving sealing of the device at a periphery thereof. Application of the force includes applying a force offset to a connection point at the device by at least one tissue apposition sustaining unit, not being a delivery shaft of the device. In this manner the protection device permits a step 804 blood flow from the aortic arch into each of the side branch vessels, but prevents emboli from entering the first and second side branch vessels without obstructing the lumen of the aortic arch.

The device 200 may be used in a method 810 for limiting the flow of emboli into the carotid arteries from the aorta, is provided. The method includes a step 811 of delivering an embolic protection device to the aortic arch to extend between the ascending aorta and the descending aorta to position the embolic protection device or components thereof into the aortic arch to prevent embolic debris to enter the carotid arteries. Further, it includes a step 812 of proximally tensioning at least one tether member distally connected to the embolic protection device, thus controlling a degree of apposition and fluid sealing of the embolic protection device against the inner vessel wall of the aortic arch.

The device 200 may be used in a method 820 for performing an endovascular procedure on a heart, is disclosed. The method includes a step 821 of delivering an embolic protection device to the aortic arch through one of the following vessels: the brachiocephalic artery from the right subclavian artery, the left carotid artery, the left subclavian artery, or the descending aorta such as in a femoral approach; or through the wall of the ascending aorta. It includes further a step 822 of positioning the embolic protection device into the aortic arch to prevent embolic debris to enter the carotid arteries. The method includes a step 823 of applying a force to the protection device for improving sealing of the device at a periphery thereof, which includes applying a force offset to a connection point at the device by at least one tissue apposition sustaining unit, not being a delivery shaft of the device. In this manner, the method allows for controlling a degree of apposition and fluid sealing of the embolic protection device against the inner vessel wall of the aortic arch by the applied force. Moreover, the method includes a step 824 of delivering a first catheter through the descending aorta, the left subclavian artery or the aortic vessel wall at the aortic arch to the heart to affect at least a step related to the endovascular procedure on the heart.

The step of applying the force may includes proximally tensioning at least one tether member distally connected to the embolic protection device.

The step of delivering the embolic protection device may be made transluminally, and delivering the first catheter may be performed after the delivering the embolic protection device.

Delivering the first catheter may include placing a balloon mounted on the first catheter with expanding the balloon in the ascending aortic arch to lock a distal end of the first catheter in place. The balloon may have a donut shape having a filter between the catheter and the inner ring of the donut shape.

The embolic protection device used in the method may extends from a distal end of a second catheter or separate channel of the first catheter, such that the position of the embolic protection device can be independently adjusted from the position of the first catheter.

Delivering a first catheter may be performed concurrently with delivering the embolic protection device via a separate channel of the first catheter, independent of the endovascular procedure.

The endovascular procedure on the heart may includes at least a step related to removal of a heart valve, the placement of a prosthetic heart valve, or repair of a heart valve. This may include the treatment of cardiac valvular disease, like valvuloplasties including percutaneous valve replacement. The procedure may be Transcatheter Aortic Heart Valve (TAVI) involving implantation of a collapsible aortic heart valve with minimally-invasive techniques.

The embolic protection device may be removed from the aortic arch following performance of the endovascular procedure.

Catheter Device Comprising Embolic Protection Unit

FIG. 16*a-c*, 17*a-c*, 18*a-c*, 19*a-b*, 20*a-c* illustrates a catheter device (500) comprising; an elongate sheath (503) with a lumen and a distal end for positioning at a heart valve (6), an embolic protection device (200) for temporarily positioning in the aortic arch for deflection of embolic debris from the ascending aorta to the descending aorta, said embolic protection device is connectable to a transluminal delivery unit (130) extending proximally from a connection point (131), and having: a frame with a periphery, a blood permeable unit within said periphery for preventing embolic particles from passing therethrough with a blood flow downstream an aortic valve into side vessels of said aortic arch to the brain of a patient, and at least one tissue apposition sustaining unit (300, 350) extending from said catheter, into said aortic arch, and being attached to said embolic protection device at a sustaining point (502), for application of a stabilization force offset to said connection point at said embolic protection device, such as at said periphery, and for providing said stabilization force towards an inner wall of said aortic arch, away from said heart, and in a direction perpendicular to a longitudinal extension of said periphery, when said catheter device is positioned in said aortic arch, such that tissue apposition of said periphery to an inner wall of said aortic arch is supported by said force for improving stability and peripheral sealing.

The stabilization force may include a tractive force and said apposition sustaining unit may comprise an active traction unit having at least one operable tether (300) distally connected at said sustaining point offset said connection point, such as to said frame, periphery and/or blood permeable unit, for providing said tractive force.

The mechanical tissue apposition sustaining unit may comprise a pushing unit (350), and said force includes a pushing force, against said frame, periphery and/or blood permeable unit, for providing said pushing force and pressing said periphery to said inner wall.

The at least one tether or pushing unit may be longitudinally elastic, whereby said force is variable for compensating physiological movements of said aortic arch relative said embolic protection device while maintaining said tissue apposition. This provides for the advantages as described above.

The blood permeable unit may have at least one guiding unit, such as an eyelet, for receiving said tether or pushing unit proximally its distal end where it is attached to said blood permeable unit, flange, or periphery. This provides for the advantages as described above.

The embolic protection device may have an attachment point where a distal end of said tether or pushing unit is connected, and optionally a radiopaque fiducial marker at said attachment point. This provides for the advantages as described above.

The tether in operation may proximally extending through an ostium into a selected side vessel such that said tractive force centers said device in relation to said ostium and pulls said device against said inner wall for locking the device in place, whereby the device is self aligning in relation to said ostium of said selected side vessel. This provides for the advantages as described above.

The catheter device may including multiple tethers distally attached along said periphery. This provides for the advantages as described above.

The frame may include at least one rib extending between different, joints at said periphery, wherein said tether or pushing unit is distally attached at said rib. This provides for the advantages as described above.

The different joints may be opposite joints. This provides for the advantages as described above.

The rib may be a yoke extending proximally above said blood permeable unit. This provides for the advantages as described above.

The yoke may extend in a longitudinal direction of at least a portion of said embolic protection device. This provides for the advantages as described above.

The catheter device may include multiple tethers, or a single tether splitting distally into multiple strands. This provides for the advantages as described above.

Two tethers or strands may be distally attached to said periphery in a Y-shape from a base of said embolic protection device. This provides for the advantages as described above.

The catheter device may include at least one eyelet, wherein one or more of said tethers or pushing unit are threaded through at least one eyelet. This provides for the advantages as described above.

One or more of said tethers may be threaded through at least one eyelet at a pivot point at a base of said device. This provides for the advantages as described above.

The blood permeable unit may be flexible, such as a flat membrane with defined porosity or holes, and said tether or pushing unit is distally attached to said membrane, such that said traction force or pushing force, when applied, raises said membrane out of a plane of said membrane. This provides for the advantages as described above.

The traction or pushing force, when applied, may raise said membrane out of a plane of said membrane, such that a volcano shape of said membrane is provided, at said attachment location of said tether or pushing unit to said membrane. This provides for the advantages as described above.

The traction unit or pushing unit may include a passive traction unit, for providing said tractive or pushing force. This provides for the advantages as described above.

The passive traction or pushing unit may be a spring, or a shape memory element. This provides for the advantages as described above.

The periphery may include a flange unit extending radially outward from said frame. This provides for the advantages as described above.

The flange unit may be angled in relation to a plane of said blood permeable unit for a pre-tension against which said stabilization force is provideable. This provides for the advantages as described above.

The tissue apposition sustaining unit may include a magnetic element and said stabilization force includes a magnetic force. This provides for the advantages as described above.

As illustrated in FIGS. 16a-c, 17a-c, 18c, 19a-b, the pushing unit comprises a distal guide element (350) connected between said sustaining point of said embolic protection device and a distal connection point (501) on said catheter, and wherein said distal guide element has a delivery state in which said embolic protection device is collapsed and substantially conforms to the sheath of said catheter, and a deployed state in which said embolic protection device is expanded whereby said periphery is substantially in said apposition with the inner wall of the aortic arch, whereby said distal guide element guides said embolic protection device towards said inner wall when moving from said delivery state to said deployed state. This provides for improved sealing of the embolic protection device against the aortic wall, since the guide element effectively guides the protection device into the right position. The movement of the guide element and the related force exerted by the same is illustrated by arrows 301, 301', in FIGS. 16b-c. Moreover the distal guide element effectively stabilizes the embolic protection device against the catheter so that misalignment is effectively prevented.

The distal guide element may be connected to a distal portion of said embolic protection device at said sustaining point. By having a support at the distal portion of the embolic protection device, as exemplified in FIGS. 16a-c, the alignment thereof can be improved. Alternatively, or in addition further guide elements (350') may be provided along the length of the embolic protection device as illustrated in FIG. 18c.

The distal guide element may comprise a shape memory material and be resiliently movable from said delivery state to said deployed state by striving towards the deployed state when being unconstrained. This provides an effective and simple deployment of the guide element and thereby the embolic protection device. A resilient guide element may allow the embolic protection filter to move in relation to the catheter device thereby following the movement of the beating heart and maintaining sealing.

Alternatively, or in addition, the distal guide element may be movable from said delivery state to said deployed state by a pushing action of said delivery unit. Thus, the delivery unit can effectively release the embolic protection device together with the guiding element for secure deployment.

The distal guide element may be pivotably movable around said distal connection point. This allows for efficient deployment way from the catheter.

The distal guide element may be formed as a support strut for said embolic protection device against said catheter. Thus enhanced support for the filter is maintained, while there is no risk of damaging the tissue which is the case with prior art devices that have stabilizing elements in direct contact with the tissue. Hence, the risk of tissue damage and release of embolies, which can occur when approaching the tissue directly with a support, is greatly reduced.

Figure 17A:
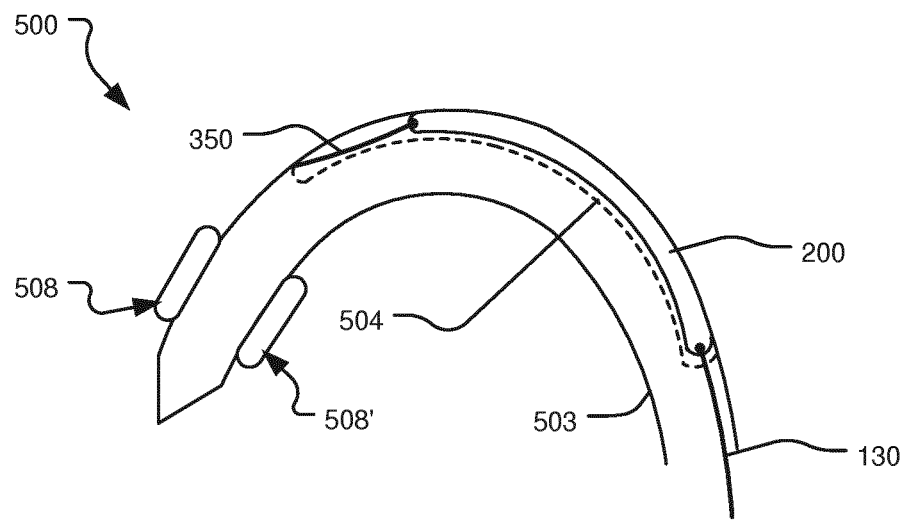
FIGS. 17a-c are schematic illustrations of a catheter device according to embodiments of the invention.

The catheter device may comprise an opening (504) through which said embolic protection device is deployable, FIG. 17a. This allows for a low profile catheter device that glides smoothly in the arch and more available space outside the catheter.

The opening may extend substantially along the length of said embolic protection device in the longitudinal direction of said sheath. This allows for an easier release of the embolic protection device.

The embolic protection device may be deliverable out of said opening by pushing of said delivery unit in the distal direction, whereby said distal guide element assumes said deployed state for guiding and supporting said frame against said wall. Thereby ease of deployment is achieved while providing for a compact and easy to use device.

The catheter device may comprise a longitudinal compartment (505) for said embolic protection device. The said embolic protection device may thus have a dedicated space before release that may ascertain that the embolic protection device is correctly positioned before release, and also avoiding interference with the other components or operating tools.

The embolic protection device may be preloaded in said longitudinal compartment. This further increases the certainty that the embolic protection device is correctly positioned and simplifies the procedure since it only needs to be expanded.

The embolic protection device may be movable from a compressed shape in said compartment through said opening. The compartment is dimensioned to fit the compressed filter and the opening may be dimensioned to both restrain the filter in the compressed shape and allow the filter to be delivered therethrough if pushed by the delivery unit, by a dilator as explained below, or by removing a restraining portion positioned over the compartment.

Figure 17B:
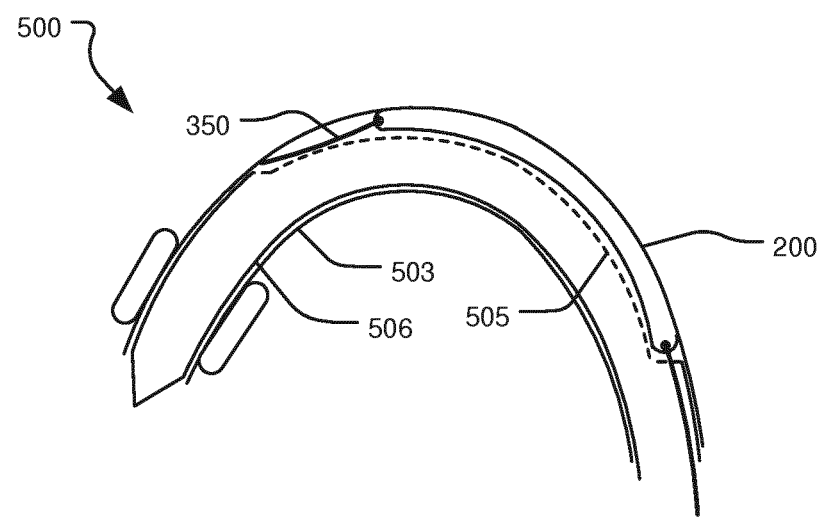

The catheter device may comprise a longitudinal dilator (506) being movable in said sheath, wherein said longitudinal compartment is arranged in said longitudinal dilator, FIG. 17b. A space for the compressed embolic protection device is thereby efficiently provided that can later be removed once the embolic protection device is deployed and the dilator is withdrawn, again allowing for a compact and easy to use catheter device.

The opening may be arranged in said sheath, and said embolic protection device may be pushable out of said longitudinal compartment through said opening when retracting said longitudinal dilator in a proximal direction. Thus, as mentioned above, release of the embolic protection device and deployment thereof, removal of the compartment, and withdrawal of the dilator is provided in a single operating step for an enhanced and more secure procedure.

Figure 17C:
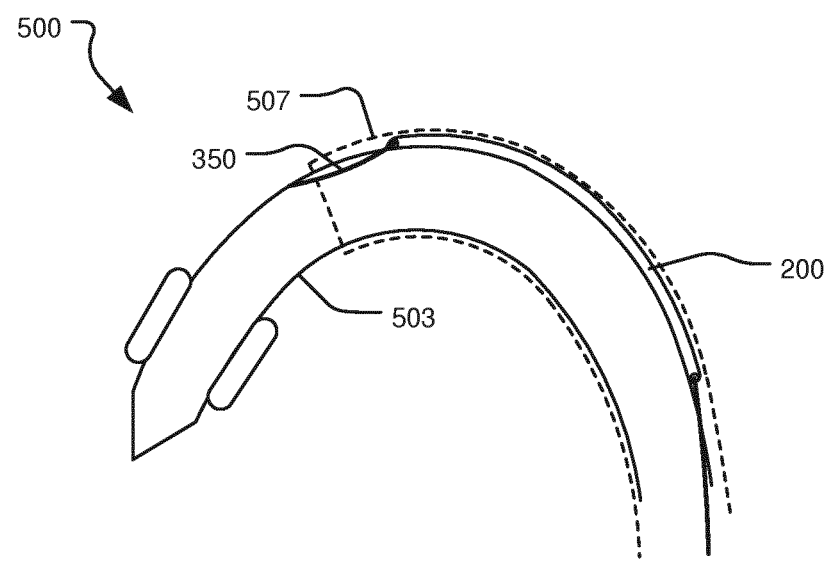
Figure 20A:
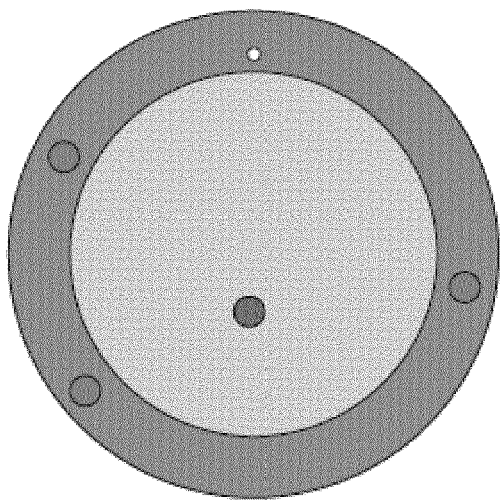
FIGS. 20a-c are schematic illustrations of a catheter device according to embodiments of the invention.
Figure 20B:
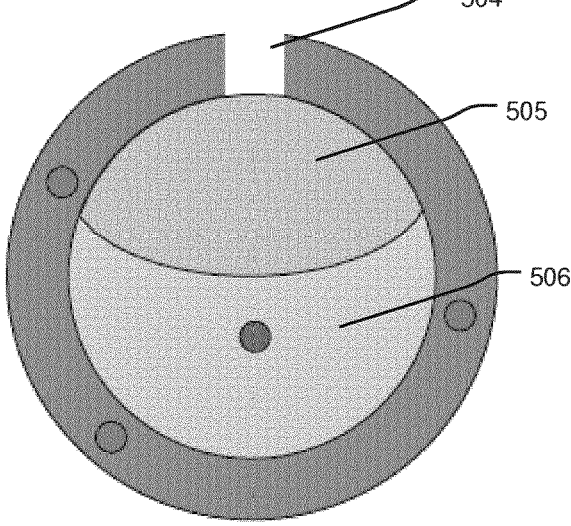
Figure 20C:
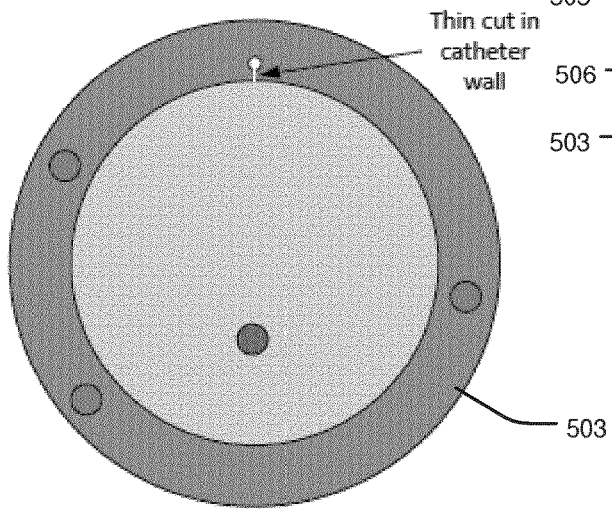

Alternatively, as illustrated in FIG. 17c, or in addition, the catheter device may comprise an outer restraining sheath (507) radially outside said sheath and being adapted to restrain said embolic protection device in a compressed shape, and being retractable to release said embolic protection device into a deployed state. This also provides an efficient way of deployment of the embolic protection device which provides of a secure procedure and increased patient safety.

The catheter device may comprise an outer restraining sheath (507) radially outside said sheath and being adapted to restrain said embolic protection device in a compressed shape, and being retractable in the proximal direction to release said embolic protection device into a deployed state, whereby said distal guide element assumes said deployed state for guiding and supporting said frame against said wall.

The catheter device may comprise a centring unit (508, 508') adapted to center said catheter in said ascending aorta, wherein said centring unit comprises a radially expandable structure. This allows correct positioning of the distal portion of the catheter over the heart, which is fundamental for performing a correct procedure. The synergetic effect of allowing for optimal positioning of the catheter while effectively protecting the side branch vessels of the aortic arch from any embolies released from the procedure is thereby provided, which optimizes and increases safety of all procedures performed through the aortic arch, and decreases the risk of later complications.

The radially expandable structure may comprise an inflatable balloon 509, 509', 509". This allows secure centering and soft apposition against the tissue.

The inflatable balloon may comprise a plurality of inflatable elements (509, 509', 509") circumferentially disposed around the radial perimeter of said catheter, as illustrated in FIG. 18b. Thus, by being circumferentially disposed, such as evenly disposed by having a similar angle between each of the inflatable elements, secure and efficient centering is provided. The device may only comprise one or two expandable elements. In this case, the expandable element may advantageously be attached to the catheter at the position 512 (FIG. 18c) which strives to push hardest against the wall of the aortic arch, when the catheter strives towards its relaxed straight shape, i.e. to the left portion (indicated by 512), of FIG. 18c. Thus, a single or a double expandable portion positioned in the vicinity of this side of the catheter, can be sufficient to push the catheter towards the center of the aortic arch. Two expandable portions may provide increased stability of the catheter position over one expandable portion. One expandable portion may occupy less space in the aortic arch. The fee space may be increased by using expanding portions that largely only expands in the radial direction, such as balloons that are shaped to be primarily elongated in the radial direction, in the inflated state, as opposed to nearly spherical shape which is the case in the FIG. 18b illustration. As mentioned below, the expandable structure may also be formed of another flexible material, such as NiTinol or plastic, discussed further below, that does not require inflation, but instead is pushed radially outwards, e.g. such as strips or bands of material that extends in the longitudinal direction of the catheter, or an expandable mesh.

The expandable structure may substantially confine to the outer surface of the catheter in a smooth manner, see illustration of FIG. 18d. This creates less friction towards the tissue wall when advancing the catheter. In case of having balloons, the balloons may be formed of a compliant material that has a very smooth surface without wrinkles when not inflated.

The plurality of inflatable elements may be individually and independently inflatable. Thus the position of the distal tip of the catheter device can be adjusted relative the heart by selectively inflating and deflating different radial elements.

The radially expandable structure 508, 508', may alternatively comprise a shape memory material, such as NiTinol or another shape memory alloy or plastic, and be resiliently movable from a compressed constrained shape to an expanded deployed state by striving towards the deployed state when being unconstrained, wherein the shape memory material is circumferentially disposed around the radial periphery of said catheter in said deployed state for centring said catheter in said ascending aorta. This provides for secure and easy centering. The outer sheath 507 or an additional outer sheath may be employed over the expandable structure to restrain expansion, and then be retracted proximally to let the expandable structure assume its expanded memory shape.

The catheter may comprise a distal centring unit (508, 508') adapted to center said catheter in said ascending aorta, and proximal centring unit (not shown) adapted to center said catheter in said descending aorta, wherein said proximal centring unit comprises a radially expandable structure. This may further improve positioning of the catheter.

The catheter device as described above may be used in transvascular delivery of a medical device to a cardiac valve region of a patient or for stabilizing an instrument for treatment thereof such as an electrophysiology procedure or an ablation procedure.

Figure 23C:
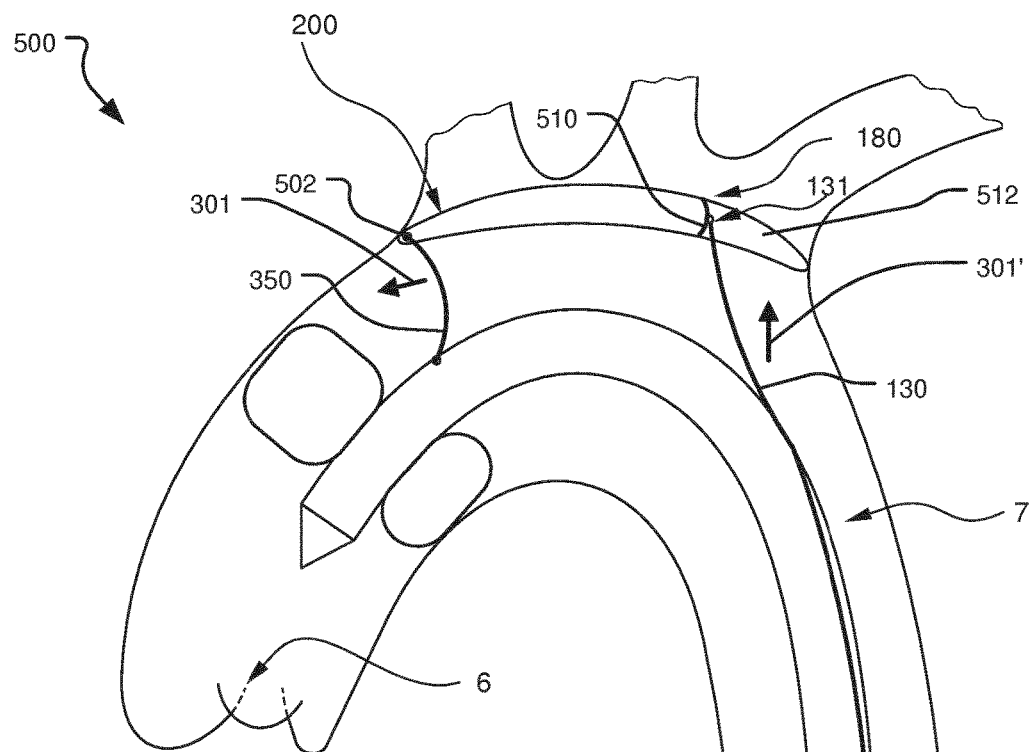
FIGS. 23a-d are schematic illustrations of a catheter device according to embodiments of the invention.
Figure 23A:
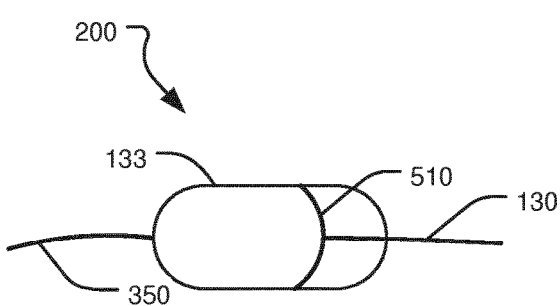
Figure 23B:
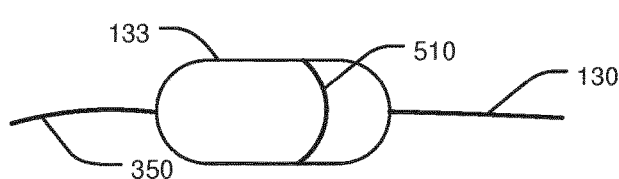

FIGS. 23a-c illustrates a central support structure 510, that extends across the frame 133. This central structure 510 may increase the apposition force against the aortic arch, and it may also support the blood permeable material itself, so that a good sealing is obtained. The central structure may extend across the frame 133 at any location between its proximal and distal end. In FIG. 23a and FIG. 23c the delivery unit 130 is connected to the central structure. This may provide for a further increased pushing force at the central part of the filter. Further, as illustrated in FIG. 23c, this allows for having a proximal extension 512 that lies in apposition with the proximal part of the tissue at the most proximal branch vessel of the aortic arch. Since there is no restraint applied to the proximal extension from the delivery unit 130, compared to the case when the delivery unit is connected to the proximal frame (FIG. 23b), the proximal extension can be allowed to be very flexible and compliant to the tissue, which increases the sealing ability.

Figure 23D:
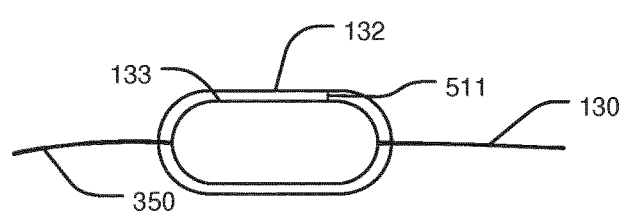

FIG. 23d illustrates that the blood permeable material 132 may extend a distance 511 beyond the frame 133. This provides an easy to manufacture device, without the need for attaching separate cushioning unit, that has the ability to allow for a soft apposition to the tissue and a god sealing ability of the device.

Figure 21:
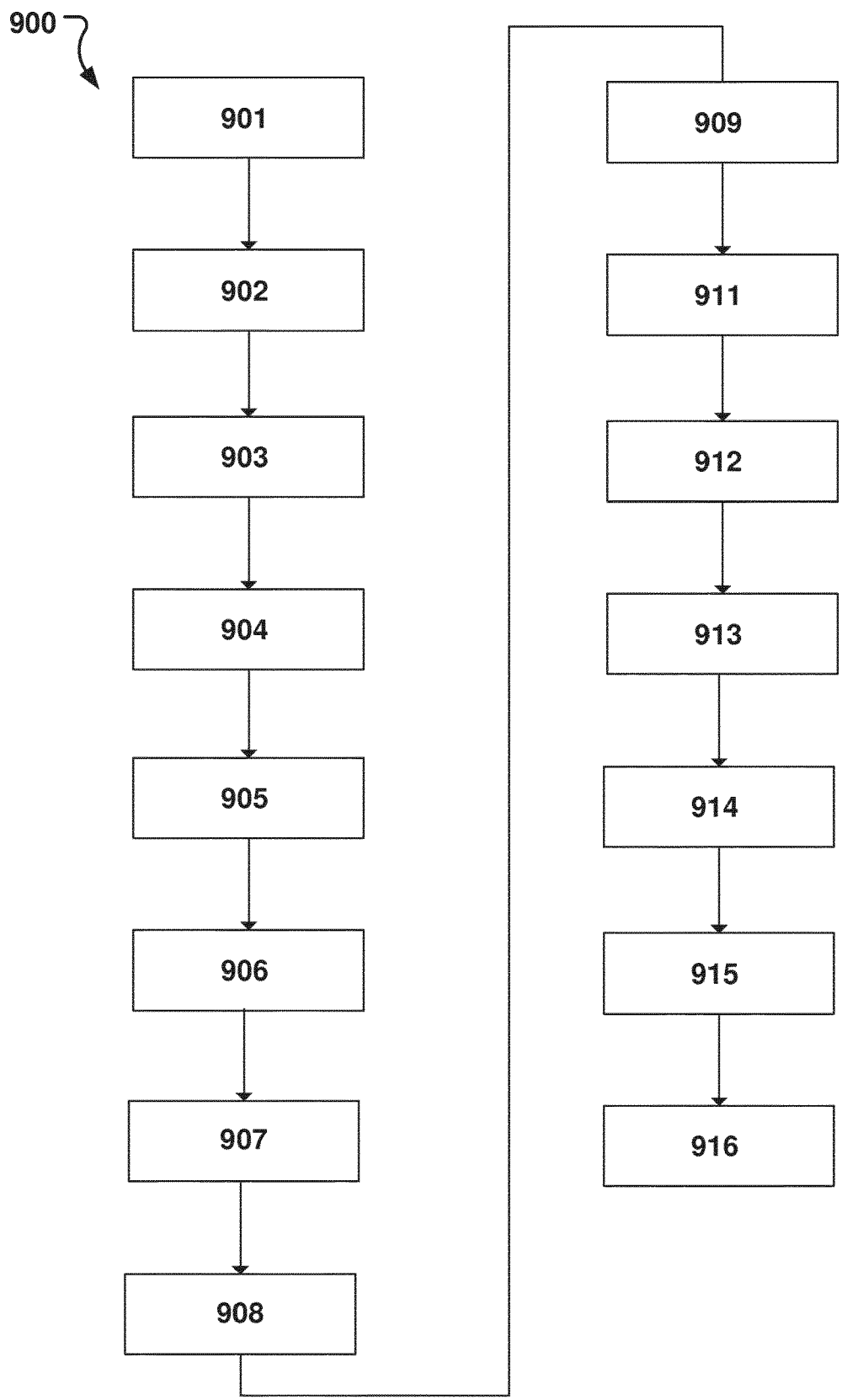
FIG. 21 is a flowchart illustrating a method according to embodiments of the invention.

FIG. 21 illustrates a method (900) of positioning an catheter device (500) in the aortic arch, comprising transluminally delivering (901) an embolic protection device (200) such as a deflector and/or filter, in the aortic arch, said embolic protection device connected to a transluminal delivery unit (130) extending proximally from a connection point (131) of said embolic protection device;

positioning (902) said embolic protection device in said aortic arch, including expanding (903) a frame of said device and flattening a blood permeable unit in said aortic arch, bringing (904) a periphery of said embolic protection device in apposition with an inner wall of said aortic arch to cover ostia of side vessels at least including the carotid arteries for preventing embolic particles from passing therethrough into side vessels to the brain of a patient; and applying (905) a stabilization force by at least one tissue apposition sustaining unit (300, 350), extending from said catheter, into said aortic arch, and being attached to said embolic protection device at a sustaining point (502), wherein said force is applied offset to said connection point at said embolic protection device, such as at said periphery, and is directed towards an inner wall of said aortic arch providing said stabilization force towards an inner wall of said aortic arch, away from said heart, and in a direction perpendicular to a longitudinal extension of said periphery, when said catheter device is positioned in said aortic arch, such that tissue apposition of said periphery to an inner wall of said aortic arch is supported by said stabilization force for improving stability and peripheral sealing.

Said supported apposition is improving apposition of said periphery to said inner wall of said aortic arch, such that said improved apposition provides for improved sealing of said periphery against said inner wall.

The method may include applying said stabilization force in a substantially proximal direction relative said device for said improved sealing.

Applying said stabilization force may include applying a tractive force by a traction unit.

The method may include, by said tractive force, pulling a periphery of said device away from said heart against said inner wall for locking the device in place in said aortic arch.

The method may include applying said tractive force by at least one tether distally connected to said frame, periphery and/or blood permeable unit for providing said tractive force.

The embolic protection device may be delivered to said aortic arch via one of said side vessels, such as the brachiocephalic artery from the right subclavian artery, the left carotid artery, the left subclavian artery, or the descending aorta such as in a femoral approach, or through the ascending aorta.

Applying said stabilization force may include applying (906) a pushing force by a pushing unit.

Applying said pushing force may comprise guiding (907) said embolic protection device from a collapsed state to a deployed state in which said embolic protection device is expanded into apposition with the inner wall of the aortic arch, by a distal guide element (350) connected between said sustaining point of said embolic protection device and a distal connection point (501) on said catheter. This provides the advantages as described above.

The method may comprise supporting (908) a distal end of said frame by said distal guide element. This provides the advantages as described above.

The method may comprise pushing (909) said embolic protection device out from a longitudinal compartment (505) in said catheter by said delivery unit, whereby said distal guide element assumes a deployed state for guiding and supporting said frame against said wall. This provides the advantages as described above.

The method may comprise pushing (910) said embolic protection device out from a longitudinal compartment (505), arranged in a dilator (506) and being movable within said catheter, when retracting said longitudinal dilator in a proximal direction. This provides the advantages as described above.

The method may comprise centering (911) said catheter in said ascending aorta with a centring unit (508, 508', 509, 509', 509") comprising a radially expandable structure. This provides the advantages as described above.

The method may comprise centering (912) said catheter with a plurality of inflatable elements (509, 509', 509") circumferentially disposed around the radial perimeter of said catheter. This provides the advantages as described above.

The method may comprise centering (913) said catheter with a shape memory material being resiliently movable from a compressed constrained shape to an expanded deployed state by striving towards the deployed state when being unconstrained, wherein the shape memory material is circumferentially disposed around the radial periphery of said catheter in said deployed state for centring said catheter in said ascending aorta. This provides the advantages as described above.

The method may comprise transvascular delivery (914) of a medical device to a cardiac valve region of a patient or stabilizing an instrument for treatment thereof such as treatment by an electrophysiology procedure (915) or an ablation procedure (916).

Figure 22A:
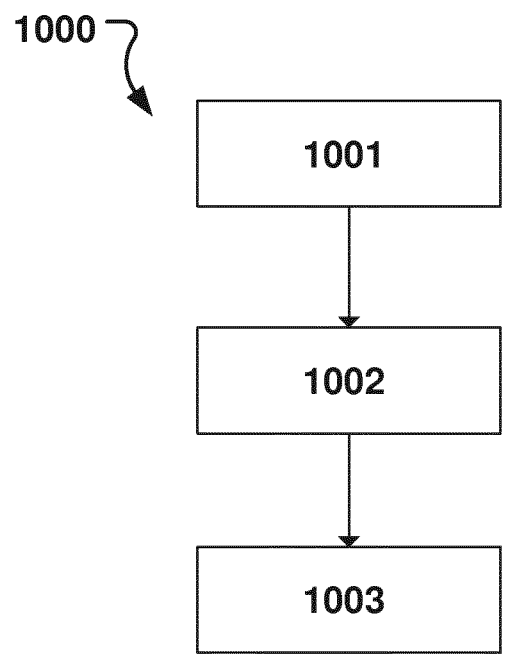
FIGS. 22a-b are flowcharts illustrating methods according to embodiments of the invention.

FIG. 22a illustrates a method (1000) of preventing emboli flowing in the aortic arch from entering side branch vessels thereof, including advancing (1001) an embolic protection to said aortic arch; and manipulating (1002) the protection device such that it covers the ostia of each of the side branch vessels, including applying (1003) a force to said protection device for improving sealing of said device at a periphery thereof, including applying a force offset to a connection point at said device by a distal guide element (350) connected between a distal sustaining point of said embolic protection device and a distal connection point (501) on a catheter, wherein the protection device permits blood flow from the aortic arch into each of the side branch vessels, but prevents emboli from entering the first and second side branch vessels without obstructing the lumen of the aortic arch.

Figure 22B:
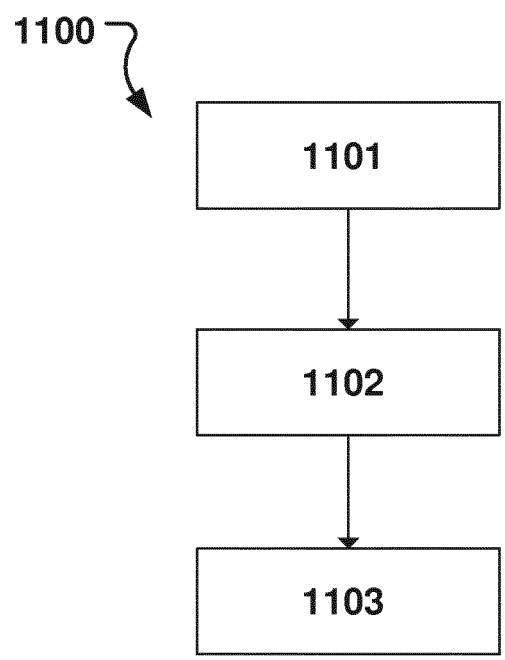

FIG. 22b illustrates a method (1100) for performing an endovascular procedure on a heart, the method including:

delivering (1101) an embolic protection device to the aortic arch through one of the following vessels: the brachiocephalic artery from the right subclavian artery, the left carotid artery, the left subclavian artery, or the descending aorta such as in a femoral approach; or through the wall of the ascending aorta; to position embolic protection device into the aortic arch to prevent embolic debris to enter the carotid arteries, applying (1101) a stabilization force to said protection device for improving sealing of said device at a periphery thereof, including applying a force offset to a connection point at said device by at least one tissue apposition sustaining unit, not being a delivery shaft of said device, thus controlling a degree of apposition and fluid sealing of the embolic protection device against the inner vessel wall of the aortic arch by said force;

and delivering (1102) a first catheter through the descending aorta, the left subclavian artery or the aortic vessel wall at the aortic arch to the heart to effect at least a step related to the endovascular procedure on the heart applying (1103) said stabilization force by tensioning at least one distal guide element (350) connected between a distal sustaining point of said embolic protection device and a distal connection point (501) on a catheter, wherein said delivering said first catheter includes placing a balloon mounted on said first catheter with expanding said balloon in the ascending aortic arch.

The balloon may be a donut shaped balloon having a filter between said catheter and the inner ring of said donut shape.

The embolic protection device may extend from a distal end of a second catheter or separate channel of said first catheter, such that the position of the embolic protection device can be independently adjusted from the position of the first catheter.

Delivering a first catheter may be performed concurrently with said delivering said embolic protection device via a separate channel of said first catheter independent of said endovascular procedure.

The endovascular procedure on the heart may include at least a step related to removal of a heart valve, the placement of a prosthetic heart valve, or repair of a heart valve.

The embolic protection device may be removed from the aortic arch following performance of the endovascular procedure.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A catheter device comprising:
an elongate sheath with a lumen and a distal end for positioning at a heart valve,
an embolic protection device for temporarily positioning across an apex of the aortic arch for deflection of embolic debris from the ascending aorta to the descending aorta, said embolic protection device is connectable to a transluminal delivery unit extending proximally from a connection point, and having:
a frame with a periphery,
a blood permeable unit within said periphery and configured for allowing blood flow to permeate therethrough while preventing embolic particles from passing therethrough downstream an aortic valve into side vessels of said aortic arch to the brain of a patient, and
at least one tissue apposition sustaining unit comprising an elongated pusher body extending from said catheter, configured to be positioned into said aortic arch, and being attached to said embolic protection device at a sustaining point located at a distal region of said embolic protection device, said pusher body configured for application of a stabilization force offset to said connection point at said embolic protection device and said pusher body configured to provide said stabilization force by pushing said embolic protection device towards side vessels of an inner wall of said aortic arch and at the same time raising a portion of said blood permeable unit out of a plane of said embolic protection device to form a dome shape, away from said heart, and in a direction perpendicular to a longitudinal extension of said periphery, when said catheter device is positioned in said aortic arch, such that tissue apposition of said periphery to an inner wall of said aortic arch is supported by said stabilization force for improving stability and peripheral sealing;
wherein said elongated pusher body is positioned in a first position when said embolic protection device is in an expanded configuration; said first position comprising said elongated pusher body extending distally out of said sheath, beneath a lateral plane of said embolic protection device opposite of said side vessels of said aortic arch, in a longitudinal direction between a proximal and a distal end of said embolic protection device relative to the elongated sheath, centrally of the blood permeable unit, and within the periphery; said elongated pusher body forcing said embolic protection unit in said direction perpendicular to a longitudinal extension of said periphery.

2. The catheter device of claim 1, wherein said blood permeable unit has at least one guiding unit comprising an eyelet and said pusher body passes through the eyelet.

3. The catheter device of claim 1, wherein said embolic protection device further comprises a radiopaque fiducial marker positioned at an attachment point of said tether pusher body to said distal region of said embolic protection device.

4. The catheter device of claim 1, said frame including at least one rib, wherein said elongated pusher body is distally attached at said rib.

5. The catheter device of claim 4, wherein said at least one rib connects between opposite joints.

6. The catheter device of claim 1, wherein said blood permeable unit is a flexible flat membrane with defined porosity or holes, and the elongated pusher body is distally attached to said membrane.

7. The catheter device of claim 1, wherein the catheter device further comprises a spring or a shape memory element configured to said elongated pusher body.

* * * * *